US012721805B2

(12) United States Patent
Rekken et al.

(10) Patent No.: US 12,721,805 B2
(45) Date of Patent: Sep. 1, 2026

(54) AMINOSILOXANE ESTER COPOLYMER AND METHODS FOR THE PREPARATION AND USE OF THE COPOLYMER

(71) Applicant: Dow Silicones Corporation, Midland, MI (US)

(72) Inventors: Brian Rekken, Midland, MI (US); Nisaraporn Suthiwangcharoen, Midland, MI (US); Anirudha Banerjee, Midland, MI (US); Zachary Wenzlick, Midland, MI (US); Dawn Carsten, Sanford, MI (US); Qian Feng, Midland, MI (US); Kimmai Nguyen, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 199 days.

(21) Appl. No.: 18/552,681

(22) PCT Filed: May 31, 2022

(86) PCT No.: PCT/US2022/072642
§ 371 (c)(1),
(2) Date: Sep. 27, 2023

(87) PCT Pub. No.: WO2023/278918
PCT Pub. Date: Jan. 5, 2023

(65) Prior Publication Data

US 2024/0180813 A1 Jun. 6, 2024

Related U.S. Application Data

(60) Provisional application No. 63/215,533, filed on Jun. 28, 2021.

(51) Int. Cl.
*A61K 8/898* (2006.01)
*A61K 8/06* (2006.01)
*A61Q 5/06* (2006.01)
*A61Q 5/12* (2006.01)
*C08G 77/452* (2006.01)

(52) U.S. Cl.
CPC ................ *A61K 8/898* (2013.01); *A61K 8/06* (2013.01); *A61Q 5/06* (2013.01); *A61Q 5/12* (2013.01); *C08G 77/452* (2013.01)

(58) Field of Classification Search
None
See application file for complete search history.

(56) References Cited

U.S. PATENT DOCUMENTS 3,958,581 A 5/1976 Abegg et al.
3,962,418 A 6/1976 Birkofer
4,009,256 A 2/1977 Nowak, Jr. et al.
4,122,029 A 10/1978 Gee et al.
4,525,521 A 6/1985 DenHartog et al.
4,697,026 A 9/1987 Lee et al.
5,136,063 A 8/1992 O'Lenick, Jr.
5,153,294 A 10/1992 O'Lenick, Jr.
5,226,923 A 7/1993 O'Lenick, Jr.
5,387,417 A 2/1995 Rentsch
5,543,074 A 8/1996 Hague et al.
5,739,192 A 4/1998 Blizzard et al.
5,804,616 A 9/1998 Mowrer et al.
5,811,487 A 9/1998 Schulz, Jr. et al.
6,177,511 B1 1/2001 Dauth et al.
6,180,117 B1 1/2001 Berthiaume et al.
7,238,768 B2 7/2007 Hupfield et al.
7,501,473 B2 3/2009 Gordon et al.
7,732,543 B2 6/2010 Loch et al.
8,193,293 B2 6/2012 Martz et al.
8,796,198 B2 8/2014 Henning et al.
8,871,888 B2 10/2014 Mowrer et al.
8,987,378 B2 3/2015 Maksimovic et al.
10,358,541 B2 7/2019 Ganachaud et al.
11,028,229 B2 6/2021 Suthiwangcharoen et al.
11,028,233 B2 6/2021 Suthiwangcharoen et al.
2004/0210074 A1 10/2004 Hupfield et al.
2004/0220306 A1 11/2004 Kageishi et al.
2011/0015332 A1* 1/2011 Martin .................... C08L 83/04 524/588
2016/0075834 A1* 3/2016 Audenaert ............... C09D 4/06 428/447
2019/0024018 A1 1/2019 Panandiker et al.

FOREIGN PATENT DOCUMENTS

| | | |
|---|---|---|
| CN | 106381084 | 2/2017 |
| DE | 19817776 | 10/1999 |
| FR | 2785179 | 5/2000 |
| JP | 2002167546 | 6/2002 |
| WO | 0151575 | 7/2001 |
| WO | 2021108068 | 6/2021 |

OTHER PUBLICATIONS

Genest "Going beyond the barriers of aza-Michael reactions: controlling the selectivity of acrylates towards primary amino-PDMS", Polym. Chem., 2016, pp. 624-630, vol. 8.
Hasegawa "Rapid Solidification of (2-Hydroxy)trimethylammonium Silicate", Chemistry Letters, 1988, pp. 1319-1322, The Chemical Society of Japan.

* cited by examiner

*Primary Examiner* — Genevieve S Alley
(74) *Attorney, Agent, or Firm* — Catherine U. Brown

(57) ABSTRACT

An aminosiloxane ester copolymer, an emulsion containing the copolymer, and processes for making the copolymer and the emulsion are provided. The copolymer and the emulsion may be formulated into hair care compositions, such as conditioners and styling products.

20 Claims, No Drawings

AMINOSILOXANE ESTER COPOLYMER AND METHODS FOR THE PREPARATION AND USE OF THE COPOLYMER

CROSS REFERENCE TO RELATED APPLICATIONS

This application is a U.S. national stage filing under 35 U.S.C. § 371 of PCT Application No. PCT/US2022/072642 filed on 31 May 2022, currently pending, which claims the benefit of U.S. Provisional Patent Application No. 63/215,533 filed 28 Jun. 2021 under 35 U.S.C. § 119 (e). PCT Application No. PCT/US2022/072642 and U.S. Provisional Patent Application No. 63/215,533 are each hereby incorporated by reference.

TECHNICAL FIELD

This invention relates to an aminosiloxane ester copolymer that is useful for hair care applications. The invention further relates to a process for making the copolymer, an emulsion containing the copolymer, and methods of use for the copolymer and the emulsion.

INTRODUCTION

Amino-functional polyorganosiloxanes, such as amine-terminated polydiorganosiloxanes are useful in hair care applications, for example, in hair conditioning applications Amine-terminated polydiorganosiloxanes made by condensation may suffer from the drawback of instability as shown by viscosity changes and/or development of an ammonia odor after aging, which is undesirable for hair care applications. Traditionally, primary amine terminated polyorganosiloxanes are expensive to make by equilibration as they require costly starting materials and catalysts and require multiple process steps to complete.

Another method for making amine-terminated polyorganosiloxanes uses allylamine- or a derivative that hydrolyzes into allylamine. These are used to do hydrosilylation chemistry with SiH terminated polymers to form the amine-terminated polyorganosiloxanes; however, this method suffers from the drawback that the amine-terminated polyorganosiloxane product may contain at least trace amounts of either SiH or allylamine, either of which would have to be removed before the product can be used in any hair care applications.

Another method of making amine-terminated polyorganosiloxanes is by ammonolysis of chloropropyl terminated siloxanes. This costly, multi-step method may suffer from the drawback of leaving residual salt (i.e., ammonium chloride) in the amine-terminated polyorganosiloxane product that may require extensive washing to remove, which is cost ineffective and poorly sustainable. Also, any residual ammonium chloride may produce a foul smell, which is undesirable for hair care applications.

Acryl functional silicone compounds and methods to prepare them have been disclosed in U.S. Pat. No. 4,697,026 to Lee, et al. Lee discloses the acryl functional silicon compounds can be prepared by intimately mixing an amino functional silicon compound having at least one primary amine or secondary amine group with an acryl functional compound having at least two acrylate, methacrylate, acrylamide, or methacrylamide groups per molecule. When amine compound and acryl compound are mixed, there is a reaction which produces an acryl functional silicon compound. This reaction is known as the Michael-type addition. Without wishing to be bound by theory, it is thought that the compounds described by Lee et al. would be unsuitable for use in hair care applications because the acrylate functionalities of those compounds can be skin sensitizers and irritants, rendering them unsuitable for hair care applications where contact with the consumer's skin and potentially accidental contact with the eye can occur.

SUMMARY

An aminosiloxane ester copolymer comprises formula:

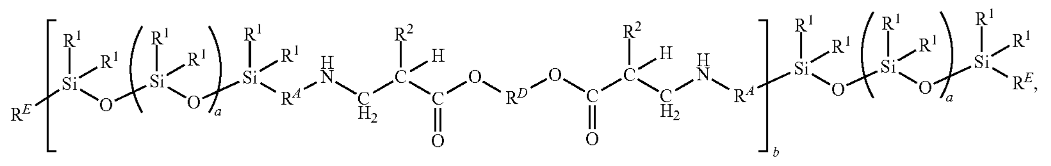

where each $R^1$ is an independently selected monovalent hydrocarbon group of 1 to 12 carbon atoms, each $R^E$ is independently selected from the group consisting of hydroxyl and an amino-functional group of formula $H_2N—R^A—$, each $R^A$ is an independently divalent hydrocarbon group of 1 to 12 carbon atoms, each $R^2$ is independently selected from the group consisting of hydrogen and methyl, each $R^D$ is an independently selected divalent hydrocarbon group of 2 to 20 carbon atoms, each subscript a independently has a value such that $0 \le a < 220$; and subscript b has a value such that $1 \le b \le 100$.

A process for preparing the copolymer comprises:

1) combining starting materials comprising (A) a terminal primary amino-functional polyorganosiloxane of formula

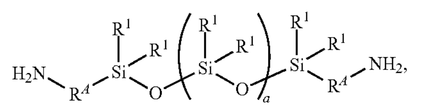

where each $R^1$ is an independently selected monovalent hydrocarbon group of 1 to 12 carbon atoms, each $R^A$ is an independently divalent hydrocarbon group of 1 to 12 carbon atoms, subscript a has a value such that $0 < a \le 220$; and (B) a bis-acryloyloxy-alkane of formula

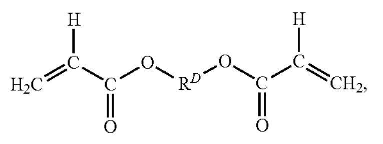

where $R^D$ is a divalent hydrocarbon group of 2 to 20 carbon atoms;

where starting material (A) and starting material (B) are present in amounts such that a molar ratio of (A):(B) ranges from 2:1 to 1:1.1. The process may further comprise preparing (A) the terminal primary amino-functional polyorganosiloxane by combining starting materials comprising:

(F) a bis-silanol-terminated polydiorganosiloxane of formula:

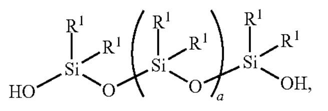

where $R^1$ and subscript a are as described above; and (G) a cyclic siloxazane of formula

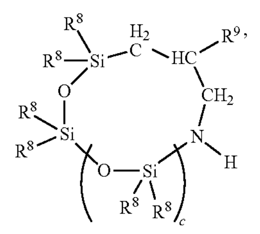

where subscript c is 0 or 1, each $R^8$ is an independently selected monovalent hydrocarbon group of 1 to 18 carbon atoms, each $R^9$ is independently selected from the group consisting of hydrogen and an alkyl group of 1 to 15 carbon atoms.

Alternatively, the process for preparing the copolymer may comprise 1) combining starting materials comprising: (F) the bis-silanol-terminated polydiorganosiloxane described above, (B) the bis-acryloyloxy-alkane described above, and (G) the cyclic siloxazane described above.

An emulsion comprises: (I) a liquid continuous phase comprising water, and (II) a discontinuous phase dispersed in the liquid continuous phase, where the discontinuous phase comprises the aminosiloxane ester copolymer described above. The copolymer and/or the emulsion described above are useful in hair care compositions.

DETAILED DESCRIPTION

The aminosiloxane ester copolymer (copolymer) comprises formula:

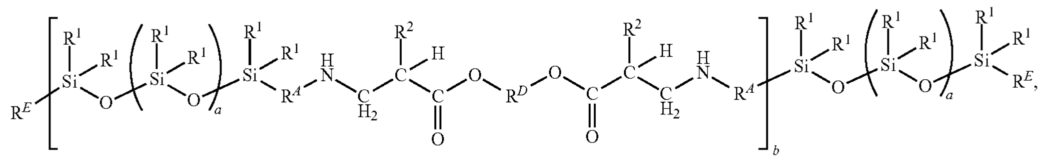

where each $R^1$ is an independently selected monovalent hydrocarbon group of 1 to 12 carbon atoms, each $R^E$ is independently selected from the group consisting of hydroxyl and an amino-functional group of formula $H_2N—R^A—$, each $R^A$ is an independently divalent hydrocarbon group of 1 to 12 carbon atoms, each $R^2$ is independently selected from the group consisting of hydrogen and methyl, each $R^D$ is an independently selected divalent hydrocarbon group of 2 to 20 carbon atoms, each subscript a independently has a value such that $0 \leq a < 220$; and subscript b has a value such that $1 \leq b \leq 100$.

Suitable monovalent hydrocarbon groups for $R^1$ include alkyl, alkenyl, aryl, and combinations thereof (e.g., aralkyl and aralkenyl). For example, suitable alkyl groups include methyl, ethyl, propyl (including iso-propyl and n-propyl), butyl (including iso-butyl, n-butyl, sec-butyl, and tert-butyl), pentyl (including linear pentyl and/or cyclopentyl) and branched alkyl groups with 5 carbon atoms, hexyl (including linear hexyl and/or cyclohexyl) and branched alkyl groups with 6 carbon atoms), octyl (including linear octyl and/or cyclooctyl), branched alkyl groups with 8 carbon atoms), decyl (including linear decyl and/or cyclodecyl) and branched alkyl groups with 10 carbon atoms, and dodecyl (including linear dodecyl and/or cyclododecyl) and branched alkyl groups with 12 carbon atoms. Alternatively, the alkyl group for $R^1$ may be selected from the group consisting of methyl and ethyl, alternatively methyl. Suitable alkenyl groups for $R^1$ include vinyl, allyl and hexenyl; alternatively vinyl or allyl; and alternatively vinyl. Suitable aryl groups for $R^1$ may include cyclopentadienyl, phenyl, naphthyl, and anthracenyl. Suitable aralkyl groups for $R^1$ include tolyl, xylyl, benzyl, 1-phenylethyl, and 2-phenylethyl. Alternatively, the aryl group for $R^1$ may be phenyl. Aralkyl groups such as benzyl, 1-phenylethyl, and 2-phenylethyl, and aralkenyl groups such as styryl, may also be used for $R^1$. Alternatively, each $R^1$ may be selected from the group consisting of methyl and phenyl. Alternatively, each $R^1$ may be methyl.

Each $R^E$ is independently selected from the group consisting of a hydroxyl group and an amino-functional group of formula $H_2N—R^A—$, where $R^A$ is a divalent hydrocarbon group. Alternatively, each $R^E$ may be hydroxyl. Alternatively, each $R^E$ may be the amino-functional group of formula $H_2N—R^A—$. Each $R^A$ is an independently selected divalent hydrocarbon group of 1 to 12 carbon atoms, alternatively 2 to 12 carbon atoms, alternatively 2 to 5 carbon atoms, and alternatively 2 to 3 carbon atoms. The divalent hydrocarbon groups for $R^A$ may be linear, branched, or cyclic, or combinations thereof. Suitable divalent hydrocarbon groups for $R^A$ include alkylene groups, arylene groups, and combinations thereof (e.g., dialkylarylene groups). The alkylene group is exemplified by ethylene, propylene, or butylene. The arylene group for $R^A$ may be arylene group such as phenylene. Alternatively, $R^A$ may be a dialkylarylene group such as:

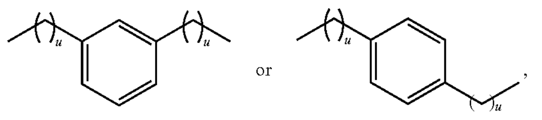

where each subscript u is independently 1 to 6, alternatively 1 to 2. Alternatively, each $R^A$ may be an alkylene group such as ethylene, propylene, or butylene; alternatively ethylene.

Each $R^2$ is independently selected from the group consisting of hydrogen and methyl. Alternatively, each $R^2$ may be hydrogen.

Each $R^D$ is an independently selected divalent hydrocarbon group of 2 to 20 carbon atoms, alternatively 2 to 12 carbon atoms, alternatively 3 to 12 carbon atoms, alternatively 4 to 12 carbon atoms, and alternatively 4 to 10 carbon atoms. The divalent hydrocarbon groups for $R^D$ may be linear, branched, cyclic, or combinations thereof. Suitable divalent hydrocarbon groups for $R^D$ include alkylene groups, arylene groups, and combinations thereof. Alternatively, each $R^D$ may be an alkylene group such as propylene, butylene, hexylene, octylene, decylene, or dodecylene; alternatively each $R^D$ may be butylene, hexylene, or decylene. Alternatively, $R^D$ may be a branched alkylene group. The arylene group for $R^D$ may be arylene group such as phenylene. Alternatively, $R^D$ may be a dialkylarylene group such as:

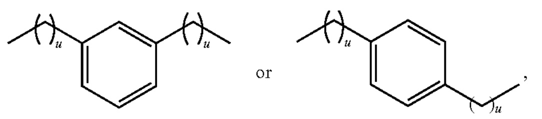

where each subscript u is independently 1 to 6, alternatively 1 to 2.

Subscript a has a value such that $0 \leq a < 220$. Alternatively, subscript a may have a value of 2 to 200, alternatively 16 to 84, alternatively 16 to 44, and alternatively, 44 to 84.

Subscript b has a value such that $2 \leq b \leq 100$. Alternatively, subscript b may have a value of 2 to 20, and alternatively 2 to 10.

The copolymer described above may have a number average molecular weight (Mn) of >1,000 g/mole to 250,000 g/mole measured by GPC according to the test method described hereinbelow. Alternatively, the copolymer may have a Mn of 4,000 g/mole to 250,000 g/mole, alternatively 4,000 g/mole to 100,000 g/mole, measured by GPC.

Alternatively, the copolymer described above may have a weight average molecular weight (Mw) of 2,000 g/mol to 400,000 g/mol. Alternatively, Mw may be 10,000 g/mol to 390,000 g/mol; alternatively 12,000 g/mol to 200,000 g/mol; alternatively 15,000 g/mol to 185,000 g/mol; alternatively 19,000 g/mol to 175,000 g/mol; alternatively 20,000 g/mol to 100,000 g/mol; alternatively 21,000 g/mol to 80,000 g/mol; alternatively 22,000 g/mol to 75,000 g/mol; alternatively 25,000 g/mol to 65,000 g/mol; alternatively 30,000 g/mol to 60,000 g/mol; alternatively 35,000 g/mol to 55,000 g/mol; and alternatively 40,000 g/mol to 50,000 g/mol.

PROCESS FOR MAKING THE COPOLYMER

The copolymer described above may be prepared by a process comprising:

1) combining starting materials comprising (A) a terminal primary amino-functional polyorganosiloxane of formula

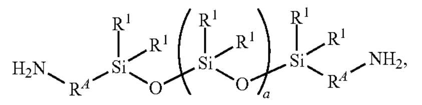

where $R^1$, $R^A$, and subscript a are as described above; and (B) a bis-acryloyloxy-alkane of formula

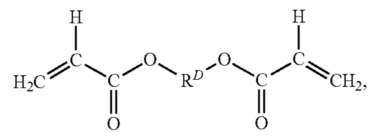

where $R^D$ is as described above; where starting material (A) and starting material (B) are present in amounts such that a molar ratio of (A):(B) ranges from 2:1 to 1:1.1; alternatively 2:1 to 1:1.05; alternatively 2:1 to 1:1. Alternatively, the molar ratio of (A):(B) may be at least 1:1, alternatively at least 1.1:1, and alternatively at least 1.3:1, while at the same time said ratio may be up to 2:1, alternatively up to 1.8:1, alternatively up to 1.5:1. The copolymer produced by this process will have amino-functional terminals, i.e., in the formula for the copolymer above, each $R^E$ will be the amino-functional group of formula $H_2N—R^A—$, as described above.

The process described above may optionally further comprise adding, during step 1), an additional starting material selected from the group consisting of: (C) a catalyst, (D) a solvent, (E) an acrylate polymerization inhibitor, and a combination of two or more of (C), (D), and (E).

Step 1) comprises mixing the starting materials, optionally with heating. Mixing in step 1) may be performed for 1 to 48 hours, alternatively 4 to 24 hours, and alternatively 6 to 15 hours. The temperature during step 1) may be 0° C. to 180° C., alternatively 20° C. to 160° C., alternatively 60° C. to 150° C., and alternatively 80° C. to 120° C. Mixing (and heating) may be performed by any convenient means, such as loading the starting materials into a vessel such as an agitated, jacketed batch reactor or reactive distillation apparatus having a jacketed reboiler, which jackets can be heated and cooled by passing steam/water or heat transfer fluid through the jacket. Step 1) may be performed under inert conditions, such as less than 3% oxygen, by purging the reactor with an inert gas, such as nitrogen. For example, step 1) may be performed under an atmosphere containing <3% oxygen when operated above 60° C. Alternatively, before heating in step 1), the process may optionally further comprise mixing the starting materials at RT for up to 60 minutes, alternatively 5 minutes to 30 minutes, and alternatively 15 minutes to 30 minutes. Without wishing to be bound by theory, it is thought that mixing at RT may facilitate coalescence of the starting materials into one phase and begin reacting (A) the terminal primary amino-functional polyorganosiloxane and (B) the bis-acryloyloxy-alkane. Furthermore, it is thought that this additional mixing step may prevent or minimize polymerization of the acrylate groups.

Starting material (A) used in the process described above is the terminal primary amino-functional polyorganosiloxane of formula

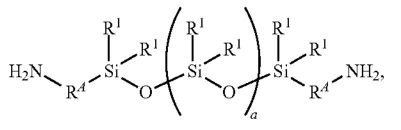

where $R^1$, $R^A$, and subscript a are as described above. Suitable terminal primary amino-functional polyorganosiloxanes are exemplified by bis-3-aminopropyl-terminated polydimethylsiloxanes, which are commercially available, e.g., under the tradename SiVance from Milliken Chemical of Spartanburg, South Carolina, USA. Terminal primary amino-functional polyorganosiloxanes may be made by known methods, such as those disclosed in U.S. Patent Application Publication 2004/0210074 to Hupfield, et al.; U.S. Pat. No. 11,028,229 to Suthiwangcharoen, et al.; U.S. Pat. No. 11,028,233 to Suthiwangcharoen, et al.; U.S. Pat. No. 7,238,768 to Hupfield and U.S. Pat. No. 8,796,198 to Henning, et al.

Starting material (B) used in the process described above is the bis-acryloyloxy-alkane of formula

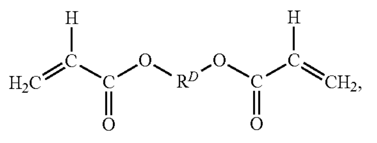

where $R^D$ is as described above. Examples of suitable bis-acryloyloxy-alkanes include 1,3-butanediol diacrylate; 1,4-butanediol diacrylate; 1,6-hexanediol diacrylate [also named 1,6-bis(acryloyloxy)hexane]; 1,9-bis(acryloyloxy) nonane; 1,10-decanediol diacrylate; and a combination thereof. Suitable bis-acryloyloxy-alkanes are known in the art and are commercially available, e.g., from various sources including Sigma-Aldrich, Inc. of St. Louis, Missouri, USA.

Starting material (C) is a catalyst that may optionally be added during the process described above. Without wishing to be bound by theory, it is thought that the catalyst may accelerate synthesis of the copolymer. When used, the catalyst is present in an amount of >0 to <90 weight % based on weights of starting materials (A) and (B) combined. The exact amount of solvent depends on the type of catalyst selected. For example, when the catalyst is an alcohol, which can also be used as a solvent, as described below, the amount of catalyst may be higher than if a different catalyst is used. For example, alcohols may be used in an amount up to 90% on the basis above, while other the other catalysts described herein may be used in an amount >0 to <5 weight % based on weights of starting materials (A) and (B) combined.

The catalyst may comprise an alcohol, a tertiary amine, pyridine, a pyridine derivative, or another aromatic heterocycle. Suitable alcohols include methanol, ethanol, isopropanol, butanol, n-propanol, and isofol-12 (2-butyl-octanol), isofol-20 (2-octyl-1-dodecanol; and INCI: Octyldodecanol. Without wishing to be bound by theory, it is thought that the longer chain alcohols, e.g., isofol-12 (2-butyl-octanol), isofol-20 (2-octyl-1-dodecanol; INCI: Octyldodecanol may act as cosolvents for the copolymer produced and may be formulated into personal care compositions. These alcohols are commercially available from Sasol of Sandton, South Africa.

Suitable tertiary amines include trimethylamine; triethylamine; tributylamine; tetramethylethylenediamine; 1,8-diazabicyclo[5.4.0]undec-7-ene (DBU); 1,5-diazabicyclo [4.3.0]non-5-ene (DBN); 1,4-diazabicyclo[2.2.2]octane (DABCO); 1,5,7-triazabicyclo[4.4.0]dec-5-ene (AKA 1,3,4, 6,7,8-Hexahydro-2H-pyrimido[1,2,-a]pyrimidine) (TBD); 7-methyl-1,5,7-triazabicyclo[4.4.0]dec-5-ene (mTBD); N-(2-hydroxyethyl)piperazine; tetramethyl guanidine (TMG); 1,2,2,6,6-pentamethylpiperidine; N-methylmorpholine (NMP); 2,2,6,6-tetramethylpiperidine (TMP); and 1-azabicyclo[2.2.2]octane. Suitable pyridine derivatives include dimethyl pyridine, e.g., 2,6-dimethylpyridine (aka 2,6-lutidine), and trimethyl pyridine. The catalysts described above are commercially available from various sources including Sigma Aldrich, Inc. and Fisher Scientific of Hampton, New Hampshire, USA.

Starting material (D) is a solvent that may optionally be added during the process described above. Suitable solvents include polydialkylsiloxanes, alcohols, aromatic hydrocarbons, aliphatic hydrocarbons, ethers, or a combination thereof. Polydialkylsiloxanes with suitable vapor pressures may be used as the solvent, and these include hexamethyldisiloxane, octamethyltrisiloxane, hexamethylcyclotrisiloxane, dodecamethylcyclohexasiloxane, tetradecamethylcycloheptasiloxane and other low molecular weight polyalkylsiloxanes, such as 0.5 to 1.5 cSt DOWSIL™ 200 Fluids and DOWSIL™ OS FLUIDS, which are commercially available from DSC.

Alternatively, starting material (D) may comprise an organic solvent. The organic solvent can be an alcohol such as methanol, ethanol, isopropanol, butanol, n-propanol, and isofol-12 (2-butyl-octanol), isofol-20 (2-octyl-1-dodecanol; and INCI: Octyldodecanol; an aromatic hydrocarbon such as benzene, toluene, or xylene; an aliphatic hydrocarbon such as heptane, hexane, octane, or isododecane; or a combination thereof. Suitable organic solvents are commercially available from various sources including Sigma Aldrich, Inc. of St. Louis, Missouri, USA.

The solvent is optional. When present, the amount of solvent will depend on various factors including the type of solvent selected and the amount and type of other starting materials selected for use in the process. However, when used, the amount of solvent may be >0% to 90%, based on combined weights of all starting materials used in step 1). The solvent may be added, for example, to aid mixing and delivery of one or more starting materials. For example, the catalyst may be delivered in a solvent. All or a portion of the solvent may optionally be removed after step 1).

Starting material (E) is an acrylate polymerization inhibitor that may optionally be added during the process described above. When present, starting material (E), the inhibitor, may be used in an amount >0 to <0.01% based on weights of starting materials (A) and (B) combined alternatively >0 to <10,000 ppm, alternatively 1 ppm to 2,000 ppm, alternatively 10 ppm to 500 ppm, on the same basis. Suitable inhibitors are commercially available, and include, for example, nitrobenzene, butylated hydroxyl toluene (BHT), diphenyl picryl hydrazyl (DPPH), p-methoxyphenol, 4-methoxy-phenol (MEHQ), 2,4-di-t-butyl catechol, phenothiazine, N,N-diethylhydroxylamine, salts of N-nitroso phenylhydroxylamine, (2,2,6,6-tetramethylpiperidin-1-yl) oxidanyl (TEMPO), and 4-hydroxy-(2,2,6,6-tetramethylpiperidin-1-yl)oxidanyl (4-hydroxy TEMPO), phenothiazine (PTZ).

One skilled in the art would recognize that certain starting materials may have more than one function. For example, the alcohol described above may function as both a catalyst and a solvent Longer chain alcohols, such as, isofol-12 (2-butyl-octanol), isofol-20 (2-octyl-1-dodecanol; and INCI: Octyldodecanol may functional as both solvents and emollient when the copolymer is formulated into a personal care product.

Alternatively, the copolymer described above may be prepared by a process comprising:

1) combining starting materials comprising:

(B) the bis-acryloyloxy-alkane as described above;

(F) a bis-silanol-terminated polydiorganosiloxane of formula:

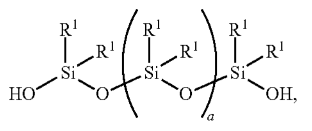

where $R^1$ and subscript a are as described above; and (G) a cyclic siloxazane of formula

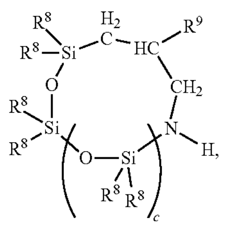

where subscript c is 0 or 1, each $R^8$ is an independently selected monovalent hydrocarbon group of 1 to 18 carbon atoms, and each $R^9$ is independently selected from the group consisting of hydrogen and an alkyl group of 1 to 15 carbon atoms. This process may optionally further comprise adding, during step 1), an additional starting material selected from the group consisting of: (C) the catalyst, (D) the solvent, (E) the acrylate polymerization inhibitor, each as described above, and a combination of two or more of (C), (D), and (E).

Step 1) comprises mixing the starting materials, optionally with heating. Mixing in step 1) may be performed for 1 to 48 hours, alternatively 4 to 24 hours, and alternatively 6 to 15 hours. The temperature during step 1) may be 0° C. to 180° C., alternatively 20 to 160, alternatively 60° C. to 180° C., and alternatively 60° C. to 150° C. Mixing (and heating) may be performed by any convenient means, such as loading the starting materials into a vessel such as an agitated, jacketed batch reactor or reactive distillation apparatus having a jacketed reboiler, which jackets can be heated and cooled by passing steam/water or heat transfer fluid through the jacket. Step 1) may be performed under inert conditions, such as less than 3% oxygen, by purging the reactor with an inert gas, such as nitrogen. For example, step 1) may be performed under an atmosphere containing <3% oxygen when operated above 60° C.

The copolymer produced by this process has terminal groups shown by $R^E$ in the formula above. The selection of the terminal groups depends on the amounts of starting materials used in the process. For example, when the molar equivalents of (B) the bis-acryloyloxy-alkane, (F) the bis-silanol-terminated polydiorganosiloxane, and (G) the cyclic siloxazane are such that less than 2 molar equivalents of (G) the cyclic siloxazane, per mole of (F) the bis-silanol-terminated polydiorganosiloxane and 0.5 molar equivalent of (B) the bis-acryloyloxy-alkane, per mole of (G) the cyclic siloxazane are used, then each $R^E$ in the formula for aminosiloxane ester copolymer may be the hydroxyl group described above. Furthermore, the amount of (B) the bis-acryloyloxy-alkane may be less than 0.5 molar equivalent of (G) the cyclic siloxazane to avoid residual acrylate functionality present in the copolymer, which may result in some of the $R^E$ groups being the amino-functional group of formula $H_2N—R^A—$ described above and some of the $R^E$ groups being hydroxyl.

Alternatively, where more than two molar equivalents of (G) the cyclic siloxazane, per mole of (F) the bis-silanol-terminated polydiorganosiloxane, then each $R^E$ may be the amino-functional group of formula $H_2N—R^A—$, as described above. Alternatively, the copolymer produced by this process may have one instance of $R^E$ being the amino-functional group and one instance of $R^E$ being the hydroxyl group in the same molecule. The amount of amino-functional groups for $R^E$ may be 0 to 100%, alternatively 0 to 50%, and alternatively 0 to 5% based on total molar amount of $R^E$ in the copolymer.

Starting material (F), the bis-silanol-terminated polydiorganosiloxane, and starting material (B), the bis-acryloyloxy-alkane, are present in amounts such that a molar ratio of (F):(B) ranges from 2:1 to 1:1.1; alternatively 2:1 to 1:1.05; alternatively 2:1 to 1:1. Alternatively, the molar ratio of (F):(B) may be at least 1:1, alternatively at least 1.1:1, and alternatively at least 1.3:1, while at the same time said ratio may be up to 2:1, alternatively up to 1.8:1, alternatively up to 1.5:1.

Starting material (F) is the bis-silanol-terminated polydiorganosiloxane of formula:

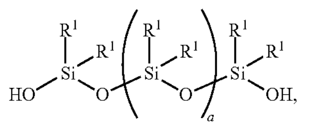

where $R^1$ and subscript a are as described above. Examples of starting material (F) include bis-silanol terminated polydimethylsiloxanes, which are known in the art and are commercially available, for example under the tradenames XIAMETER™ OHX from DSC. Bis-silanol terminated polydiorganosiloxanes suitable for use as starting material (F) may be prepared by methods known in the art, such as hydrolysis and condensation of the corresponding organohalosilanes or equilibration of cyclic polydiorganosiloxanes.

Starting material (G) is the cyclic siloxazane of formula:

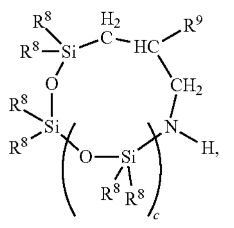

where subscript c is 0 or 1, each $R^8$ is an independently selected monovalent hydrocarbon group of 1 to 18 carbon atoms, and each $R^9$ is independently selected from the group consisting of hydrogen and an alkyl group of 1 to 15 carbon atoms. Each $R^9$ is independently selected from the group consisting of hydrogen and an alkyl group of 1 to 15 carbon atoms, alternatively 1 to 12 carbon atoms, and alternatively 1 to 6 carbon atoms. Suitable alkyl groups are exemplified by methyl, ethyl, propyl (e.g., iso-propyl and/or n-propyl), butyl (e.g., isobutyl, n-butyl, tert-butyl, and/or sec-butyl), pentyl (e.g., isopentyl, neopentyl, and/or tert-pentyl), hexyl, heptyl, octyl, nonyl, and decyl, as well as branched saturated monovalent hydrocarbyl groups of 6 or more carbon atoms including cycloalkyl groups such as cyclopentyl and cyclohexyl. Alternatively, each alkyl group for $R^9$ may be methyl. Alternatively, each $R^9$ may be a hydrogen atom. Alternatively, at least one $R^9$ per molecule may be an alkyl group such as methyl.

Each $R^8$ is an independently selected monovalent hydrocarbon group of 1 to 18 carbon atoms. The monovalent hydrocarbon group is exemplified by an alkyl group, an aryl group, and an aralkyl group. Alternatively, the monovalent hydrocarbon group may be an alkyl group. s for $R^8$ are exemplified by those described above for $R^9$.

Examples of suitable cyclic siloxazanes include:

1,1,3,3,-tetramethyl-2-oxa-7-aza-1,3-disilacycloheptane of formula

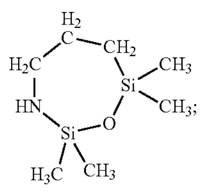

and 1,1,3,3,5,5-hexamethyl-2,4-di-oxa-9-aza-1,3,5-trisilacyclononane of formula

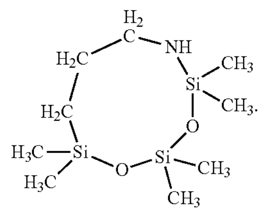

The cyclic siloxazane may be prepared by a hydrosilylation reaction of an allyl-functional amine and an SiH-terminated siloxane oligomer in the presence of a hydrosilylation reaction catalyst and a hydrosilylation reaction promoter, as described in U.S. Provisional Patent Application Ser. No. 62/940,414 filed on 26 Nov. 2019 to Rekken, et al., which is hereby incorporated by reference.

In the process described above, (B) bis-acryloyloxy-alkane, (F) the bis-silanol-terminated polydiorganosiloxane, and (G) the cyclic siloxazane may be combined concurrently, or in any order, in step 1). Without wishing to be bound by theory, it is thought that when starting materials (B), (F), and (G) are combined concurrently, (G) the cyclic siloxazane will first react with the silanol groups of starting material (B) to form a terminal primary amino-functional polydiorganosiloxane in situ, which will subsequently undergo an aza-Michael addition with the (B) the bis-acryloyloxy-alkane. The inventors surprisingly found that (B) the bis-acryloyloxy-alkane did not readily react with the secondary amine functionality of the cyclic siloxazane. Alternatively, in step 1), starting material (G), the cyclic siloxazane, and starting material (F), the bis-silanol-terminated polydiorganosiloxane, may be combined to form an amino-functional polyorganosiloxane, and thereafter starting material (B), the bis-acryloyloxy-alkane, may be added. Without wishing to be bound by theory, it is thought that (G) the cyclic siloxazane does not readily react with (B) the bis-acryloyloxy-alkane. The process for forming (A) the terminal primary amino-functional polyorganosiloxane may comprise i) combining starting materials comprising: (G) the cyclic polysiloxazane described above, (F) the bis-silanol-terminated polydiorganosiloxane described above, and optionally ii) recovering (A) the primary amino-functional polyorganosiloxane. This process may be performed as described in U.S. Provisional Patent Application Ser. No. 62/940,414 filed on 26 Nov. 2019 to Rekken, et al. by selecting a bis-silanol-terminated polydiorganosiloxane corresponding to starting material (F) above for use in the process.

Step i) (combining starting materials comprising (G) and (F)) in the process for forming (A) the primary amino-functional polyorganosiloxane may be performed by any convenient means, such as mixing, optionally with heating. Mixing and heating may be performed using any convenient means, such as loading the starting materials into a vessel such as an agitated, jacketed batch reactor or reactive distillation apparatus having a jacketed reboiler, which jackets can be heated and cooled by passing steam/water or heat transfer fluid through the jacket. The process may be performed at a temperature of at least 50° C., alternatively at least 85° C., and alternatively at least 90° C. Alternatively, heating in step i) may be performed at 50° C. to 150° C., alternatively 85° C. to 150° C., and alternatively 90° C. to 150° C. The process is performed for a time sufficient to form (A) the terminal primary amino-functional polyorganosiloxane. In step i), one of (G) the cyclic siloxazane and (F) the bis-silanol-terminated polydiorganosiloxane may be added continuously or in increments into a vessel containing the other of (F) and (G). Such addition may be performed manually or using metering equipment. The process for forming (A) the primary amino-functional polyorganosiloxane described above may optionally further comprise one or more additional steps. This process may optionally further comprise step iii) adding one or more additional starting materials to the reaction mixture in step i). Alternatively, step iii) may be performed during and/or after step i) and before step ii). The additional starting material may be selected from the group consisting of an acid precatalyst, an aminoalkyl-functional alkoxysilane, an endblocker, a solvent as described above for starting material (D), and a combination of two or more of thereof, as described in U.S. Provisional Patent Application Ser. No. 62/940,414 filed on 26 Nov. 2019 to Rekken, et al. The resulting primary amino-functional polyorganosiloxane may be used in the process as described above to make the aminosiloxane ester copolymer described above.

In the process for making the aminosiloxane ester copolymer described above, the process may optionally comprise one or more additional steps. The processes may further comprise: 2) recovering the aminosiloxane ester copolymer (during and/or after step 2). Recovery may be performed by any convenient means, such as stripping and/or distillation with heating and optionally with reduced pressure; and/or removing (C) the catalyst, e.g., by stripping and/or distillation, neutralization, when catalyst is used, and/or adsorption. Furthermore, one skilled in the art would recognize that in the process described above, when (G) the cyclic siloxazane is used, an alcohol is not used as (C) the catalyst and (D) the solvent when (G) the cyclic siloxazane is present, so as to avoid reaction of the alcohol with the cyclic siloxazane to generate an alkoxy-functional aminofunctional alkoxysilane or siloxane.

EMULSION COMPRISING THE COPOLYMER

The copolymer described above may be formulated in an emulsion. The emulsion may comprise: (I) a liquid continuous phase comprising water, and (II) a discontinuous phase dispersed in the liquid continuous phase, where the discontinuous phase comprises the aminosiloxane ester copolymer described above. The amount of copolymer added to the emulsion can vary and is not limited. However, the amount typically may range from a weight ratio of copolymer/emulsion of 1 to 70%, alternatively 2 to 60%. Water (and additional starting materials, if present) may constitute the balance of the emulsion to 100%.

Water

The water is not generally limited, and may be utilized neat (i.e., absent any carrier vehicles/solvents), and/or pure (i.e., free from or substantially free from minerals and/or other impurities). For example, the water may be processed or unprocessed prior to making the emulsion described herein. Examples of processes that may be used for purifying the water include distilling, filtering, deionizing, and combinations of two or more thereof, such that the water may be deionized, distilled, and/or filtered. Alternatively, the water may be unprocessed (e.g. may be tap water, i.e., provided by a municipal water system or well water, used without further purification). Alternatively, the water may be purified before use to make the emulsion.

Additional Starting Materials

The emulsion described above may further comprise an additional starting material selected from the group consisting of a (H) surfactant, (I) an acid compound, (J) an acid anhydride, (K) a thickener, (L) a stabilizer, (M) a preservative, and a combination of two or more of (H), (I), (J), (K), (L), and (M).

The copolymer described above may be self-emulsifying (i.e., a separate surfactant is optional). However, when used, the surfactant may be anionic, cationic, nonionic, or amphoteric, or a combination of two or more thereof. The amount of surfactant may be 2% to 25% based on combined weights of all starting materials in the emulsion.

(H) Surfactant

The anionic surfactant may selected from alkali metal sulforicinates, sulfonated glyceryl esters of fatty acids, salts of sulfonated monovalent alcohol esters, amides of amino sulfonic acids, sulfonated products of fatty acids nitriles, sulfonated aromatic hydrocarbons, condensation products of naphthalene sulfonic acids with formaldehyde, sodium octahydroanthracene sulfonate, sodium lauryl sulfate, alkali metal alkyl sulfates, alkyl ether sulfates having at least 8 carbon atoms, alkyl aryl ether sulfates, alkylarylsulfonates having at least 8 carbon atoms, alkylbenzenesulfonic acids, salts of alkylbenzenesulfonic acids, sulfuric esters of polyoxyethylene alkyl ether, amine salts or sodium salts or potassium salts of alkylnaphthylsulfonic acid, and combinations thereof. Suitable anionic surfactants are commercially available from various sources including sodium lauryl sulfate, which is available from Pilot under the tradename CALIMULSE™ SLS. Other anionic surfactants commercially available from TDCC, include alkyldiphenyloxide disulfonate salts, which are available under the tradename DOWFAX™; dioctyl sulfosuccinates, which are available under the tradename TRITON™ GR; phosphate esters, which are available under the tradename TRITON™ H-55, H-65, QS-44, OR XQS-20; sulfates and sulfonates, which are available under the tradename TRITON™ QS-15 and TRITON™ XN-45S.

The cationic surfactant may be selected from dodecylamine acetate, octadecylamine acetate, acetates of the amines of tallow fatty acids, homologues of aromatic amines having fatty acids, fatty amides derived from aliphatic diamines, fatty amides derived from aliphatic diamines, fatty amides derived from disubstituted amines, derivatives of ethylene diamine, quaternary ammonium compounds, salts of quaternary ammonium compounds, alkyl trimethylammonium hydroxides, dialkyldimethylammonium hydroxides, coconut oil, methylpolyoxyethylene cocoammonium chloride, dipalmitoylethyl hydroxyethylmonium methosulfate, amide derivatives of amino alcohols, amine salts of long chain fatty acids, and combinations thereof. Cationic surfactants are commercially available from various sources including dialkylmethyl quaternary ammonium compounds (e.g., cetrimonium chloride) under the tradename ARQUAD™ from Akzo Nobel; ADOGEN™ cationic surfactants from Evonik; TOMAH™ cationic surfactants from Tomah Products, Inc. of Milton, Wisconsin, USA; and VARIQUAT™ cationic surfactants from Sea-Land Chemical Company of Westlake, Ohio, USA.

The nonionic surfactant may be selected from alkylphenol alkoxylates, ethoxylated and propoxylated fatty alcohols, alkyl polyglucosides and hydroxyalkyl polyglucosides, sorbitan derivatives, N-alkylglucamides, alkylene oxide block copolymers, such as block copolymers of ethylene oxide, propylene oxide and/or butylene oxide, fatty alcohol polyglycolethers, polyhydroxy and polyalkoxy fatty acid derivatives, amine oxides, silicone polyethers, various polymeric surfactants. Nonionic surfactants are commercially available, for example, alkylphenol alkoxylates are available under the tradename ECOSURF™ EH; secondary alcohol ethoxylates, nonylphenol ethoxylates, and ethylene oxide/propylene oxide copolymers are commercially available under the tradename TERGITOL™; and specialty alkoxylates such as amine ethoxylates and octylphenol ethoxylates are available under the tradename TRITON™, all from TDCC. Alternatively, the nonionic surfactant may be, e.g., trideceth-6 or trideceth-12, which are available under the tradename SYNPERONIC™ from Croda or LUTENSOL™ from BASF. Alternatively, the nonionic surfactant may be e.g., a fatty alcohol polyglycol ether such as GENAPOL™ UD 050, and GENAPOL™ UD110, which are commercially available from Clariant of Frankfurt, Germany.

The nonionic surfactant may also be a silicone polyether (SPE). The silicone polyether as an emulsifier may have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure. Suitable silicone polyethers include Dow Silicones™ 5329 from DSC. Alternatively, the nonionic surfactant may be selected from polyoxyalkylene-substituted silicones, silicone alkanolamides, silicone esters and silicone glycosides. Such silicone-based surfactants are known in the art, and have been described, for example, in U.S. Pat. No. 4,122,029 to Gee et al., U.S. Pat. No. 5,387,417 to Rentsch, and U.S. Pat. No. 5,811,487 to Schulz et al.

Suitable amphoteric surfactants include betaines such as alkyl(C12-14)betaine, cocoamidopropylbetaine, cocoamidopropyldimethyl-hydroxysulphobetaine, dodecylbetaine, hexadecylbetaine, and tetradecylbetaine; sultaines such as cocamidopropylhydroxysultaine; lecithin; hydrogenated lecithin; cocoamphodiacetates; cocoiminodipropionate; and dodecyliminodipropionate.

The emulsion may be formed as a water-in-oil emulsion (w/o), which contains a water-in-oil surfactant, (which may subsequently inverted by addition of more water). The water-in-oil surfactant may be nonionic and may be selected from polyoxyalkylene-substituted silicones, silicone alkanolamides, silicone esters and silicone glycosides, as described above. Alternatively, when the emulsion is an oil-in-water (o/w) emulsion, it may include nonionic surfactants known in the art to prepare o/w emulsions. Suitable nonionic surfactants for this embodiment are exemplified by the polyoxyethylene alkyl ethers, polyoxyethylene alkylphenol ethers, polyoxyethylene lauryl ethers, polyoxyethylene sorbitan monooleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants, as described above.

(I) Acid Compound

The acid compound may optionally be added to the emulsion described herein for adjusting pH. Suitable acids include acetic acid, formic acid, propionic acid, and combinations thereof. Suitable acids for adjusting pH are disclosed, for example, in U.S. Pat. No. 6,180,117.

Method for Making the Emulsion

Emulsions may be prepared in a batch, semi-continuous, or continuous process using conventional equipment. For example, mixing the starting materials to form the emulsion may occur, for example using, batch equipment with high-shear and high-speed dispersers include those made by Charles Ross & Sons (NY), Hockmeyer Equipment Corp. (NJ); batch mixing equipment such as those sold under the tradename Speedmixer™; batch equipment with high shear actions include Banbury-type (CW Brabender Instruments Inc., NJ) and Henschel type (Henschel mixers America, TX). Illustrative examples of continuous mixers/compounders include extruders, such as single-screw, twin-screw, and multi-screw extruders, co-rotating extruders, such as those manufactured by Krupp Werner & Pfleiderer Corp (Ramsey, NJ), and Leistritz (NJ); twin-screw counterrotating extruders, two-stage extruders, twin-rotor continuous mixers, dynamic or static mixers or combinations of these equipment.

The starting materials described above may be combined under any suitable conditions for forming an emulsion. For example, to simplify the mixing process and keep the emulsion viscosity low while handling, any acid compound may be added at the end of the method, i.e., once the desired dilution level is reached.

Hair Care

The copolymer, and the emulsion comprising the copolymer, each as described above, are useful in hair care compositions. The hair care composition may be a conditioner and/or leave in hair treatment, such as a styling product. The hair care composition can be used for purposes such as styling (e.g., curl retention) and/or conditioning of the hair fibers.

The use of the hair care composition according to the invention may use a conventional manner for conditioning hair. For example, an effective amount of the composition for conditioning hair is applied to the hair. Such effective amounts generally range from 0.5 g to 50 g, alternatively from 1 g to 20 g. Application to the hair typically includes working the composition through the hair such that most or all of the hair is contacted with the product. This method for conditioning the hair comprises the steps of applying an effective amount of the hair care composition to the hair, and then working the composition through the hair. These steps can be repeated as many times as desired to achieve the desired conditioning benefit.

Non-limiting examples of additives which may be formulated into the hair conditioner composition in addition to the copolymer and/or emulsion described above: (i) a chelating agent, (ii) deposition agents such as cationic deposition aids, (iii) additional emulsifiers (e.g., nonionic), (iv) fragrances, (v) oils, (vi) pigments, (vii) preservatives, (viii) stabilizing agents, (ix) thickeners, and combinations thereof.

The hair care composition may contain at least one cationic deposition aid, alternatively a cationic deposition polymer. The cationic deposition aid may be present in amounts ranging from 0.001% to 5%, alternatively 0.01% to 1%, and alternatively 0.02% to 0.5% based on total weight of all ingredients in the personal care product. The cationic deposition polymer may be a homopolymer or be formed from two or more types of monomers. The molecular weight of the cationic deposition polymer may be at least 10,000, alternatively may range from 5,000 to 10,000,000, alternatively, and alternatively 100,000 to 2,000,000. The cationic deposition polymers will have cationic nitrogen containing groups such as quaternary ammonium or protonated amino groups, or a mixture thereof. The cationic charge density may be at least 0.1 meq/g, alternatively above 0.8 or higher. The cationic charge density should not exceed 4 meq/g, it is alternatively less than 3; and alternatively less than 2 meq/g. The charge density can be measured using the Kjeldahl method and should be within the above limits at the desired pH of use, which may range from 3 to 9; alternatively 4 to 8. The cationic nitrogen-containing group will generally be present as a substituent on a fraction of the total monomer units of the cationic deposition polymer. Thus when the cationic deposition polymer is not a homopolymer it can contain spacer noncationic monomer units. Such polymers are described in the CTFA Cosmetic Ingredient Directory, 3rd edition. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers may have alkyl groups of 1 to 7 carbon atoms, alternatively alkyl groups of 1 to 3 carbon atoms. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, alternatively tertiary may be used. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers may be lower alkyls such as the alkyl groups of 1 to 4 carbon atoms, alternatively alkyl groups of 1 to 2 carbon atoms. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide. The cationic deposition aids can comprise mixtures of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, NJ, USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, NJ, USA) under the GAFQUAT tradename (e.g., GAFQUAT 755N); cationic diallyl quaternary ammonium-containing polymer including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256 to Nowak Jr., et al.; and cationic polyacrylamides as described in U.S. Pat. No. 5,543,074 to Hague et al. Other cationic deposition aids that can be used include polysaccharide polymers, such as cationic cellulose derivatives and cationic starch derivatives. Cationic polysaccharide polymer materials suitable for use in compositions of the invention include those of the formula: —O($R^{15}$—N+$R^{16}R^{17}R^{18}$X—) wherein: A is an anhydroglucose residual group, such as starch or cellulose anhydroglucose residual, $R^{15}$ is an alkylene oxyalkylene, polyoxyalkylene, or hydroxyalkylene group, or combination thereof, $R^{16}$, $R^{17}$ and $R^{18}$ independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in $R^{16}$, $R^{17}$ and $R^{18}$) may 20 or less, and X is an anionic counterion, as previously described. Cationic cellulose is available from Amerchol Corp. (Edison, NJ, USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, NJ, USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418 to Birkofer, incorporated by reference herein), and copolymers of etherified cellulose and starch (e.g., as described in U.S. Pat. No. 3,958,581 to Abegg et al., incorporated by reference herein).

The hair care composition may contain various additional oils. The term "oil" as used herein refers to any material which is substantially insoluble in water. Suitable oils include, but are not limited to, natural oils such as coconut oil; hydrocarbons such as mineral oil and hydrogenated polyisobutene; fatty alcohols such as octyldodecanol and cetearyl alcohol (which is commercially available under the tradename Crodacol CS-50); esters such as C12-C15 alkyl benzoate; diesters such as propylene dipelargonate; and triesters, such as glyceryl trioctanoate and silicones especially cyclomethicone and dimethicone and mixtures thereof. The hair care composition may also contain oils, alternatively a mixture of low viscosity and high viscosity oils. Suitable low viscosity oils have a viscosity of 5 to 100 mPa·s at 25° C., and may be esters having the structure $R^{20}$CO—$OR^{21}$ wherein $R^{20}$CO represents the carboxylic acid radical and wherein $OR^{21}$ is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., alternatively a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. Alternatively, argan oil may be used. The suggested ratio of low viscosity to high viscosity oils in the oil phase is 1:15 to 15:1, alternatively 1:10 to 10:1 respectively. Alternatively, the personal care product may comprise 1% to 20% of a mixture of low viscosity and high viscosity surface oils.

Among the additional oils, mineral oils, such as liquid paraffin or liquid petroleum, of animal oils, such as perhydrosqualene, or alternatively vegetable oils, such as sweet almond, calophyllum, palm, castor, avocado, jojoba, olive or cereal germ oil may be added to a hair care composition containing the copolymer described above. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

A thickening agent may be added to provide a convenient viscosity. For example, viscosities of 500 $mm^2/s$ to 25,000 $mm^2/s$ at 25° C. or alternatively 3,000 to 7,000 $mm^2/s$ are usually suitable. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, hydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or mixtures of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. Thickening agents are commercially available, e.g., hydroxyethylcellulose is available under the tradename Cellosize™ hydroxyethyl cellulose PCG-10 Europe from TDCC. The thickening agent may be used in a hair care composition in an amount sufficient to provide a viscosity of 500 $mm^2/s$ to 25,000 $mm^2/s$. Alternatively the thickening agent may be present in an amount from 0.05% to 10% and alternatively 0.05% to 5% based on the total weight of the hair care composition.

Stabilizing agents can be used in the water phase of the hair care composition containing the copolymer described above. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it may amount to 0.1% to 5% and alternatively 0.5% to 3% of the total composition. The hydrocolloids include gums, such as Xanthan gum or Veegum and thickening agents, such as carboxymethyl cellulose. Polyols, such as glycerine, glycols, and sorbitols can also be used. Alternative polyols are propylene glycol, sorbitol and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and xanthan gum.

The hair care composition may optionally further comprise a chelating agent, e.g., tetrasodium ethylenediaminetetraacetic acid (tetrasodium EDTA), which is commercially available under the tradename Versene 220.

The hair care composition may optionally further comprise an additional emulsifier. The additional emulsifier may be a nonionic emulsifier, (e.g., PEG-100 Stearate & Glyceryl Stearate).

The hair care composition may optionally further comprise a preservative. Examples of suitable preservatives include Phenoxyethanol and Methylisothiazolinone, which are commercially available as Neolone PE Preservative.

The hair care composition can also be under the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

When selecting ingredients for the hair care composition described above, there may be overlap between types of ingredients because certain ingredients described herein may have more than one function. For example, hydroxyethylcellulose may be useful as a colloidal stabilizer and a thickening agent. When adding additional ingredients to the hair care composition, the additional ingredients are distinct from one another.

Alternatively, the hair care product may be a hair conditioner comprising:

(I) the copolymer described above, or the emulsion of the copolymer described above, (II) water, optionally (ix) a thickener (e.g., Hydroxyethyl-cellulose), (v) an oil, such as a fatty alcohol (e.g., Cetearyl Alcohol), optionally (iii) other emulsifiers (e.g., PEG-100 Stearate & Glyceryl Stearate), optionally (vii) a preservative, and optionally (ii) a cationic deposition aid, and optionally (i) a chelating agent (e.g., tetrasodium ethylenediaminetetraacetic acid).

Alternatively, the emulsion described above may be used as a leave in hair treatment composition (e.g., styling aid).

EXAMPLES

The following examples are intended to illustrate the invention and are not to be construed as limiting to the scope of the invention set forth in the claims. Certain starting materials used in the Examples are described in Table 1 below, followed by characterization and evaluation procedures also used in the Examples.

TABLE 1

| Starting Materials | | |
|---|---|---|
| Starting Material | Description | Source |
| TAS 1 | Aminopropyl-terminated polydimethylsiloxane with DP = 44 | DSC |
| TAS 2 | Aminopropyl-terminated polydimethylsiloxane with DP = 16 | DSC |
| TAS 3 | Aminopropyl-terminated polydimethylsiloxane with DP = 84 | DSC |
| TAS 4 | Aminopropyl-terminated polydimethylsiloxane with DP = 225 | DSC |
| TAS 5 (from DOE table, Table 5) | Aminopropyl-terminated polydimethylsiloxane with DP = 319 | DSC |
| TAS 6 | Aminopropyl-terminated polydimethylsiloxane with DP = 2 | DSC |
| OH-PDMS | bis-silanol-terminated polydimethylsiloxane with DP = 40 | XIAMETER ™ PMX-0156 |
| BAA 1 | 1,6-hexanediol diacrylate | Alfa Aesar |
| BAA 2 | 1,4-butanediol diacrylate | TCI Chemicals |
| BAA 3 | 1,10-decanediol diacrylate | TCI Chemicals |
| BAA 4 | 1,4-butanediol di(meth)acrylate | Millipore-Sigma |
| BAA 5 | 1,6-hexanediol di(meth)acrylate | Millipore-Sigma |
| Catalyst 1 | 1,8-Diazabicyclo[5.4.0]undec-7-ene (DBU) | Millipore-Sigma |
| Catalyst 2 | 2,6-lutidine | Millipore-Sigma |

As used herein, materials branded XIAMETER™ are commercially available from DSC.

In this Reference Example 1, copolymers were prepared as follows. A terminal primary aminofunctional polyorganosiloxane and a bis-(acryloyloxy) alkane were combined and mixed for 30 minutes under an inert atmosphere (i.e., with oxygen content <3%). The resulting mixture was heated to 80-90° C. over 1 hour. The mixture was then heated to 90-120° C. and optionally stirred for a period of time (A hours in Table 2, below). The mixture was then heated to 130° C. to 150° C. and optionally stirred for a period of time (B hours in Table 2, below). Examples 1p and 1q demonstrated that even if residual acrylate remained after heating, the acrylate was consumed over a period of days or weeks even at ambient temperature. The resulting copolymers were characterized by a combination of $^{1}H$ NMR, $^{13}C$ NMR, $^{29}Si$ NMR, IR, rheometry (viscosity), and/or GPC. Evaluation of the Storage Modulus (G') and the Loss Modulus relative to Frequency, ω, rad/s, did not show them to cross in the most acrylate-rich example (1a), indicating little to no cross-linking of the polymers.

TABLE 2

| Preparation of Copolymers according to Reference Example 1 | | | | | | | |
|---|---|---|---|---|---|---|---|
| Sample | TAS | BAA | Ratio of TAS/BAA | Mixing Time A (hours) | Mixing Time B (hours) | Viscosity (mPa · s) | Mw (g/mole) |
| 1a | 1 | 1 | 1/1 | 24 | 8 | 27000 | 79520 |
| 1b | 1 | 1 | 1.1/1 | 31 | 0 | 23389 | 51800 |
| 1c | 2 | 1 | 1/1 | 30 | 0 | Highly viscous liquid | 181712 |
| 1d | 1 | 1 | 1.3/1 | 2 | 2 | 702 (4572-2 years)[3] | 30861 |
| 1e | 1 | 1 | 1.15/1 | 3 | 16 | 5550 | 31250 |
| 1f | 3 | 1 | 1.3 | 15 | 6 | 8860 | 61030 |
| 1g | 1 | 3 | 1.3/1 | 5 | 8 | 3936 | 22574 |
| 1h (8800-1) | 1 | 3 | 1.3/1 | 4 | 9 | 480 | 27990 |
| 1i (8800-2) | 1 | 1 | 1.3/1 | 2 | 8 | 420 | 19650 |
| 1j (8800-3) | 1 | 2 | 1.3/1 | 2 | 12 | 640 | 19780 |
| 1k (8800-4) | 1 | 1 | 1.1/1 | 5 | 18 | 3300 | 48060 |
| 1l (9818) | 1 | 1 | 1.5/1 | 8 | 0 | 700 | 15550 |
| 1m (8800-11) | 1 | 1 | 2/1 | 2 | 0 | 460 | 10240 |
| 1n (8800-12) | 3 | 1 | 1.5/1 | 12 | 0 | 2020 | 35690 |
| 1o (8800-8) | 2 | 1 | 1.3 | 2 | 0 | 1905 | 12520 |
| 1p (8815) | 1 | 1 | 1.3 | 3[1] | 2 | 2143 | 29831 |

TABLE 2-continued

Preparation of Copolymers according to Reference Example 1

| Sample | TAS | BAA | Ratio of TAS/BAA | Mixing Time A (hours) | Mixing Time B (hours) | Viscosity (mPa · s) | Mw (g/mole) |
|---|---|---|---|---|---|---|---|
| 1q (8818-1) | 1 | 2 | 1.3 | 4[2] | 0 | 1057 | 22591 |
| 1r (2227) | 3 | 1 | 1.3 | 22 | 0 | 3355 | 41822 |

[1]Denotes that Sample 1p was mixed for an additional four days at ambient temperature.

[2]Denotes that Sample 1q was mixed for an additional twenty five days at ambient temperature.

[3]Denotes that this sample had viscosity of 702 when initially tested and viscosity of 4572 after aging for two years. The data in Table 1 show that copolymers can be made according to the method of this invention exemplified by the procedure in Reference Example 1 without catalyst. The Storage Modulus and Loss Modulus data indicated that the copolymers were linear and did not suffer from the drawback of crosslinking, which is a problem with amine-containing-hydrocarbon polymers that use Aza-Michael Addition reactions with bis(acryloyloxy)alkanes to form a comparative polymer backbone.

In this Comparative Example 2, TAS 4 was combined with BAA 1. These two liquids were miscible when mixed at ambient temperature for 30 minutes, and then a catalytic amount of 2,6-lutidine (ca. 400 ppm) was added. The resulting reaction mixture was heated to 80° C. for 2 hours, and then 90° C. for 5.5 hours, to give a clear solution that was cooled to ambient temperature and stirred. However, within 24 hours, the mixture had fallen apart to give a suspension of solid polymerized acrylates and terminal amino-functional polydimethylsiloxane.

In this Comparative Example 3, Comparative Example 2 was repeated, and split into two batches with a DBU catalyst added to one. Within 30 hours, both mixtures fell apart to give a suspension of solid polymerized acrylates and terminal amino-functional polydimethylsiloxane.

Comparative Examples 2 and 3 showed that when a terminal primary amino-functional polyorganosiloxane with DP that was too high was used, a copolymer could not be formed under the conditions tested.

In this Reference Example 4, copolymers were prepared as follows: A terminal primary aminofunctional polyorganosiloxane and a bis-(acryloyloxy)-alkane were combined and mixed for 30 minutes under an inert atmosphere (i.e., with oxygen content <3%). A catalyst (2,6-lutidine) was added, and the resulting mixture was heated to 90° C. over 1 hour. The mixture was then heated to 110° C. and optionally stirred for a period of time (Mixing Time A hours in Table 3, below). The mixture was then heated to 140° C. to 150° C. and optionally stirred for a period of time (B hours in Table 3, below). If any residual acrylate was still present in the resulting product, it would be consumed over time under ambient conditions. The resulting copolymers were characterized by a combination of $^1$H NMR, $^{13}$C NMR, $^{29}$Si NMR, IR, rheometry (viscosity), and/or GPC.

TABLE 3

Copolymers Prepared According to Reference Example 4

| Sample | TAS | BAA | Ratio of TAS/BAA | Catalyst amount (ppm) | Mixing Time A (hours) | Mixing Time B (hours) | Viscosity (mPa · s) | Mw (g/mole) |
|---|---|---|---|---|---|---|---|---|
| 4a | 1 | 1 | 1/1 | 600 | 13[1] | | 11,748 | 33,064 |
| 4b | 1 | 1 | 1/1.05 | 600 | 5 | 6.5 | 65,640 | 170,730 |
| 4c | 3 | 1 | 1.5/1 | 600 | 17 | 6 | 10,050 | 50,120 |
| 4d | 3 | 1 | 1.2/1 | 600 | 6 | 10 | 37095 | 72,233 |
| 4e | 3 | 1 | 1.3/1 | 300 | 2 | 14 | 3200 | 52,720 |
| 4f | 3 | 1 | 1.1/1 | 600 | 18 | 10 | Forms a gum[2] | 48,580; initially; 389,120 after 22 mo |

[1]Denotes that Sample 4a was held for 13 hours at 90° C. instead of heating as described above. After heating, there was significant amounts of residual acrylate; however, upon sitting for 22 months, the material increased in viscosity.

[2]Sample 4f was too viscous to measure with the same instrument used for the other samples. Sample 4f became stringy after aging for 21 months. Sample 4f had MW = 389, 121; Mn = 41462; and PD = 9.39.

In this Example 5, 45.00 g (113 mmol) of the bis (aminopropyl)tetrasiloxane, 1,13-diamino-4,4,6,6,8,8,10,10-octamethyl-5,7,9-trioxa-4,6,8,10-tetrasilatridecane, was added to a 250 mL reaction flask with a magnetic stir bar and thermocouple. The flask was inerted and under a flow of $N^2$, 19.74 g (87 mmol) of BAA1 was added over 15 minutes. Due to the reaction exotherm, the mixture temperature rose from ca. 22° C. to 39° C. and the clear and colorless liquid became significantly more viscous. The mixture was stirred at ambient temperature for another ca. 8 hours. $^1$H, $^{13}$C, and $^{29}$Si NMR analysis confirmed that the acrylate (BAA1) was consumed. GPC revealed that the material had an weight average molecular weight of 4130 g/mol. This example showed that a process to an (AB)n copolymer using a siloxane oligomer (DP=2) could be performed using the method of this invention even without external heating. A substantial exotherm was observed, and the product produced was viscous (4150 mPa·s) compared to the product made with the TAA having DP=16 or DP=44.

A 3-component, single reactor process was developed for making $(AB)_n$ copolymers. The process involved adding a bis-silanol-terminated polydiorganosiloxane, a bis-acryloyloxy-alkane, and a cyclic siloxazane (1,1,3,3,-tetramethyl-2-oxa-7-aza-1,3-disilacycloheptane) shown below in Scheme 1, to form copolymers such as those described in Reference Examples 1 and 4. Without wishing to be bound by theory, it is thought that the cyclic siloxazane will first react with the bis-silanol-terminated polydiorganosiloxane to form the bis(aminopropyl)siloxane in situ, which will subsequently undergo an aza-Michael 1,4-addition with the bis-acryloyloxy-alkane. Surprisingly, the bis-acryloyloxy-alkane used under the conditions tested did not readily react with the secondary amine present in the cyclic siloxazane. When the cyclic siloxazane and the bis-acryloyloxy-alkane were combined in a mixture, no reaction was observed when heated to 60° C. for ca. 3 hours in the presence of 1.2% 2,6-lutidine catalyst. The cyclic siloxazane began reacting with the bis-silanol-terminated polydiorganosiloxane immediately concluding within 6-8 hours at ambient temperature and less at elevated temperature as disclosed in PCT Publication WO2021/108068 corresponding to U.S. Provisional Patent Application Ser. No. 62/940,414 filed on 26 Nov. 2019 to Rekken, et al. Without wishing to be bound by theory, it is thought that the method provided herein will involve initial addition of the cyclic siloxazane to the bis-silanol-terminated polydiorganosiloxane followed by an aza-Michael addition, as illustrated below in Scheme 1.

ture, resulting in a mild exotherm, indicating a reaction. After the exotherm subsided, the mixture was stirred at ambient temperature for 2 hours, where it had become notably more viscous, and then slowly raised the pot temperature to 80° C. over one hour, then heated at 80° C. for three hours, then 120° C. for three hours and then 70° C. for two hours. $^{1}H$ and $^{29}Si$ NMR spectroscopy and viscosity measurement supported the formation of a material akin to that in Example 1i.

When the cyclic siloxazane was combined with the bis-silanol-terminated polydiorganosiloxane so that there was less than 2 moles cyclic-siloxazane (Y) per mole of silanol (X) on the bis-silanol-terminated polydiorganosiloxane, and the moles of bis-acryloyloxy-alkane (Z) were equal to half the moles of the cyclic siloxazane (Y), an $(AB)_n$ copolymer was formed where the copolymer was terminated by SiOH functionality (rather than having primary amino propyl groups) as shown in Scheme 2. When the copolymer will be used in a hair care composition, Z may be selected to be less than Y/2 to minimize or avoid the potential of residual Scheme 1.

(top) addition of cyclic siloxazane did not readily react with a bis-acryloyloxy-alkane. (bottom) In a mixture, the bis-silanol-terminated polydiorganosiloxane will react with the cyclic siloxazane and subsequently with the bis-acryloyloxy-alkane, regardless of the order of addition.

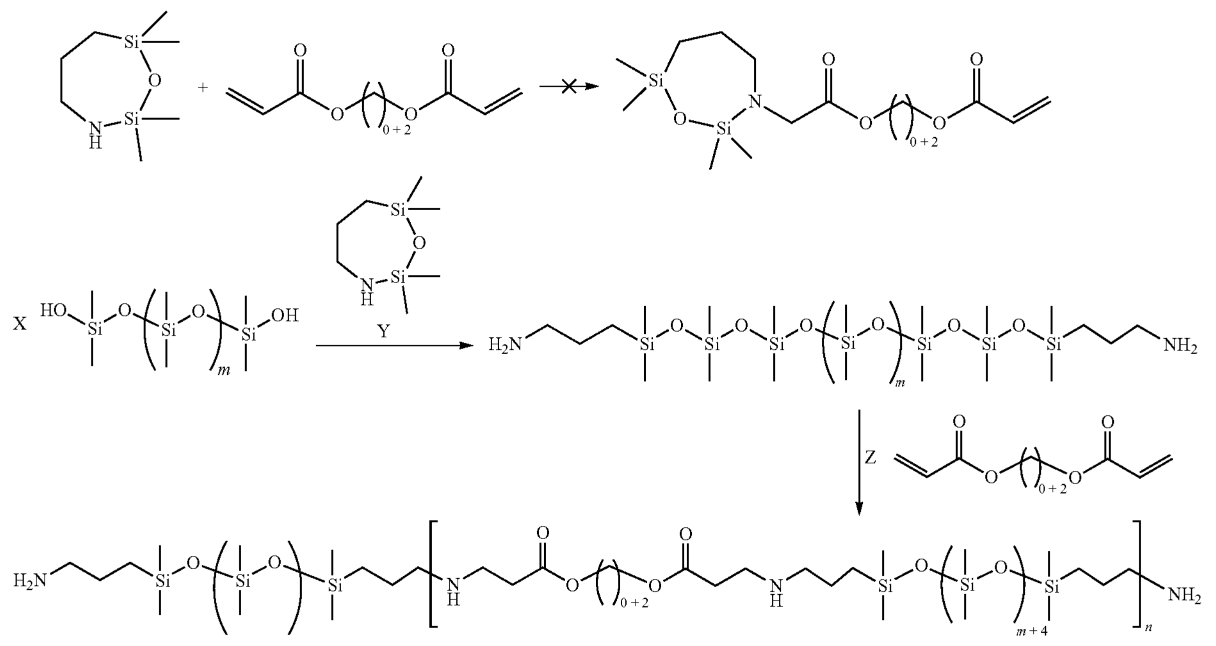

In this Example 6, 80.1 g (25.6 mmol) of OH-PDMS was added to a 3-neck, 250 mL reaction flask with a gas inlet, an air-cooled condenser fed to an oil bubbler, a glass stopper, and a magnetic stir bar. While mixing, 4.51 g (19.9 mmol) of BAA1 was added to the mixing OH-PDMS and stirred for ca. 5 minutes. The atmosphere was inerted below 0.3% oxygen. Then, 10.4 g (54.9 mmol) of 1,1,3,3,-tetramethyl-2-oxa-7-aza-1,3-disilacycloheptane was added to the mixacrylate in the copolymer, which can results in a small amount of amino-functional-terminated $(AB)_n$ copolymer in the mixture. This can include $(AB)_n$ copolymers with silanol termination on one end and an amino-functional group on the other. The amount of residual amino-functional terminated $(AB)_n$ copolymer can be 0 to <100%; alternatively, 0 to 50%; and alternatively, 0 to 5%.

Scheme 2. Method for making oligosiloxane, bis-aminoester-alkane, $(AB)_n$ copolymers with silanol termination.
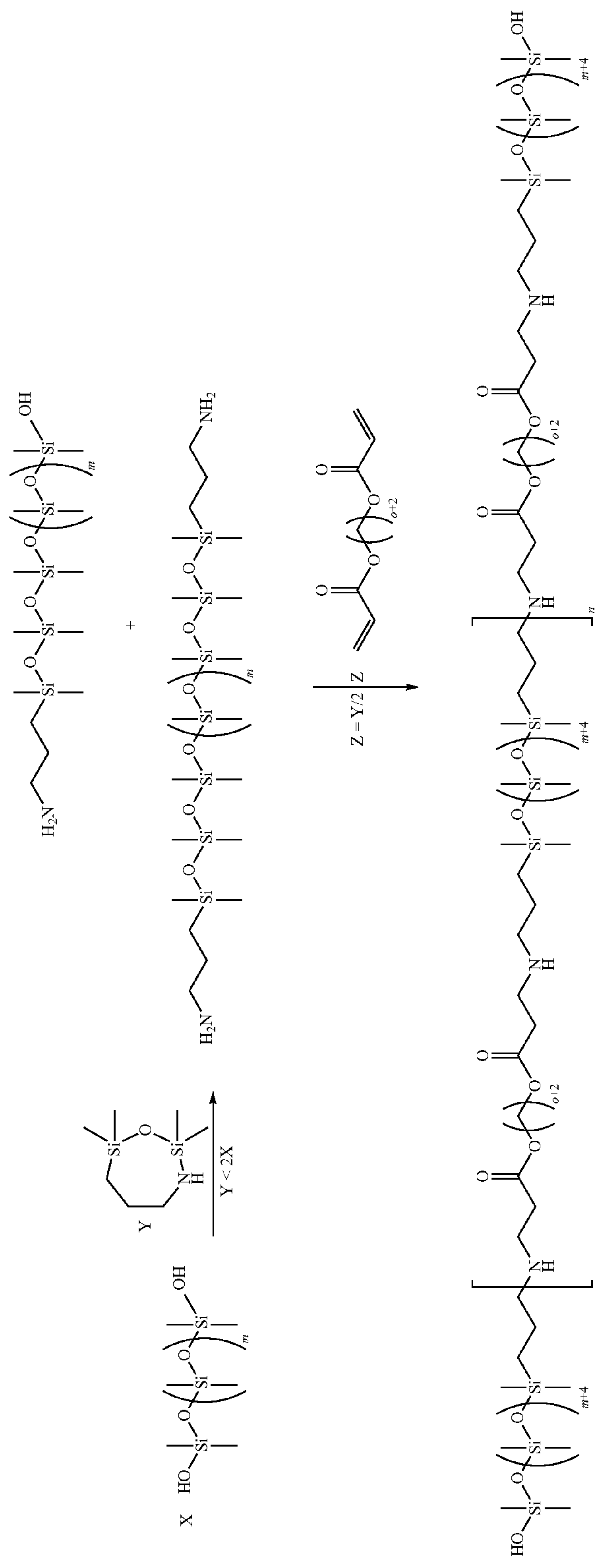

In this Example 7, 80.1 g (25.6 mmol) of OH-PDMS was added to a 3-neck, 250 mL reaction flask with a gas inlet, an air-cooled condenser fed to an oil bubbler, a glass stopper, and a magnetic stir bar. While mixing, 4.51 g (19.9 mmol) of BAA1 was added to the mixing OH-PDMS and stirred for ca. 10 minutes. The atmosphere was inerted below 0.3% oxygen. Then, 7.81 g (41.2 mmol) of 1,1,3,3,-tetramethyl-2-oxa-7-aza-1,3-disilacycloheptane was added to the mixture, resulting in a mild exotherm, indicating a reaction. After the exotherm subsided, the mixture was stirred at ambient temperature for 1.5 hours, where it had become notably more viscous, and then raised the pot temperature to 60° C. and stirred for 1.5 hours, then heated at 80° C. for 6 hours to give a polymer with a viscosity of 755 mPa·s and an average molecular weight of 19940 g/mol. The product was also characterized by $^{1}H$, $^{13}C$, and $^{29}Si$ NMR spectroscopy.

In this Comparative Example 8, derivative polymers of Reference Examples 1 and 4 were attempted to be synthesized using similar conditions and using alkanediol di(meth) acrylates, BAA4 and BAA5, in place of alkanediol acrylates. The conversion was extremely sluggish taking weeks to complete even 50% conversion. Neither alkanediol (meth)acrylate BAA4 nor BAA5, undergo complete conversion when combined with either TAS 1 or TAS 2, when the TAS was used in either a 30% or 100% molar excess. Furthermore, addition of the catalyst, DBU (ca. 2000 ppm), improved the conversion rate slightly, but was not able to achieve complete conversion in a multiweek time frame heating up to 120° C. Furthermore, the beginning of the process was not comparable as inerting the reaction flask and heating to 60° C. in at least less than one hour lead to polymerization of the methacrylate moieties and separation from the polyorganosiloxane matrix, as initiated by the formation of a hazy white solid. Without a process to remove the methacrylate moieties in the product, these copolymers would not be suitable for any personal care application due to the skin-sensitizing properties of the methacrylate functional starting material.

In this Reference Example 9, emulsions of the copolymer samples prepared as described above were prepared using the starting materials and amounts shown below in Table 4. Amounts are weight per cents. Samples were prepared as follows: Copolymer, surfactant and water were added in a 100 DAC cup. These starting materials were speed mixed in a Speed Mixer twice at 3500 RPM, 30 seconds each time. The resulting mixture was diluted with the remaining amount of water stepwise with speed mixing at 3500 RPM for 30 seconds between each successive water dilution step. Acetic acid was added to this mixture and the components were speed mixed at 3500 RPM for an additional 30 seconds.

TABLE 4

| | Emulsion Samples | | | | |
|---|---|---|---|---|---|
| Sample | Emulsion 5a | Emulsion 5b | Emulsion 5c | Emulsion 5d | Emulsion 5e |
| Copolymer 1g in Table 2 | 25% | 0 | 0 | 0 | 0 |
| Copolymer 4b (18) in Table 3 | 0 | 23% | 0 | 0 | 0 |
| Copolymer 1f in Table 2 | 0 | 0 | 24.9% | 0 | 0 |
| Copolymer 4c in Table 3 | 0 | 0 | 0 | 24.4% | 0 |
| Copolymer 4a (17) | 0 | 0 | 0 | 0 | 25% |
| nonionic surfactant | 12.5% | 12% | 12.4% | 12.8% | 12.5% |
| DI H2O | 62.50% | 64.87% | 62.57% | 62.67% | 62.50% |
| Acetic Acid | 0.18% | 0.13% | 0.13% | 0.13% | 0.13% |
| total | 100% | 100% | 100% | 100% | 100% |
| PS D(v, 50) nm | 57.6 | 96.4 | 176 | 44.8 | 42 |
| PS D(v, 90) nm | 92.5 | 160 | 240 | 117 | 129 |

In this Reference Example 10, emulsions of the copolymer samples prepared as described above were prepared using the starting materials and amounts shown below in Table 5. Samples were prepared as follows: Copolymer, surfactants, and water were added in a 100 DAC cup. These starting materials were speed mixed in a Speed Mixer twice at 3500 RPM, 30 seconds each time. The resulting mixture was diluted with the remaining amount of water stepwise with speed mixing at 3500 RPM for 30 seconds between each successive water dilution step. Non-ionic surfactants were used to make the emulsions. The surfactants used were S1 and S2 from Table 6.

TABLE 5

Emulsion Samples Prepared According to Reference Example 6

| | Emulsion ref | | | |
|---|---|---|---|---|
| | EM1 | EM6 | EM5 | EM4 |
| Si wt % | 60% | 60% | 60% | 60% |
| Surfactant wt % | 6.1% | 6.1% | 6.3% | 6.1% |
| Dv10 (um) | 0.194 | 0.0595 | 0.182 | 0.168 |
| Dv50 (um) | 0.252 | 0.163 | 0.33 | 0.296 |
| Dv90 (um) | 0.558 | 0.361 | 0.517 | 0.457 |

| | Emulsion ref | | |
|---|---|---|---|
| | EM3 | EM7 | EM9 |
| Si wt % | 60% | 60% | 60% |
| Surfactant wt % | 5% | 5% | 5% |
| Dv10 (um) | 0.152 | 0.155 | 0.186 |
| Dv50 (um) | 0.269 | 0.287 | 0.339 |
| Dv90 (um) | 0.419 | 0.458 | 0.538 |

| | Emulsion ref | | |
|---|---|---|---|
| | EM8 | EM10 | EM2 |
| Si wt % | 25% | 25% | 25% |
| Surfactant wt % | 12.5% | 12.9% | 13.7% |
| Dv10 (um) | 0.0996 | 0.1323 | 0.126 |
| Dv50 (um) | 0.1374 | 0.2102 | 0.1689 |
| Dv90 (um) | 0.2454 | 0.325 | 0.2275 |

In this Reference Example 11, emulsions were made with anionic, cationic, and non-ionic surfactants. The starting materials used are in Table 6.

| Starting Material for Emulsions | INCI name, if any | Label | Role | Source |
|---|---|---|---|---|
| Copolymer sample 1h | | P1 | Copolymer | Synthesized as described in Table 2 |
| Copolymer sample 1p | | P2 | Copolymer | Synthesized as described in Table 2 |
| Copolymer sample 1k | | P3 | Copolymer | Synthesized as described in Table 2 |
| Copolymer sample 1q | | P4 | Copolymer | Synthesized as described in Table 2 |
| Copolymer sample 1r | | P5 | Copolymer | Synthesized as described in Table 2 |
| Copolymer sample #6# | | P6 | Copolymer | Synthesized as described in Example 6 |
| Copolymer sample #7# | | P7 | Copolymer | Synthesized as described in Example 7 |
| Synperonic 13/6 | Trideceth-6 | S1 | Non-ionic Surfactant | Croda |
| Synperonic 13/12 | Trideceth-12 | S2 | Non-ionic Surfactant | Croda |
| Calimulse SLS | Sodium Lauryl Sulfate | S3 | Anionic Surfactant | Pilot |
| Arquad 16-29 | Cetrimonium Chloride | S4 | Cationic Surfactant | AkzoNobel |
| Lutensol TO6 | Trideceth-6 | S5 | Non-ionic Surfactant | BASF |
| 10% Acetic acid | Aqueous acetic acid | A1 | Acid | Sigma |
| Water | DI water | D1 | Diluent | DSC |

Emulsion Samples were prepared using the starting materials described in the amounts below in Tables 7-8. Amounts of each starting material are in weight parts unless otherwise indicated. Table 7 shows non-ionic emulsions. Table 8 shows anionic and cationic emulsions.

TABLE 7

| Non-ionic Emulsions | | | | | | | | |
|---|---|---|---|---|---|---|---|---|
| Starting | Emulsion No. | | | | | | | |
| Material | EM12 | EM16 | EM17 | EM21 | EM22 | EM23 | EM24 | EM25 |
| P1 | 2 | 0 | 0 | 0 | 0 | 0 | 0 | 0 |
| P2 | 0 | 0 | 3.6 | 0 | 19.99 | 0 | 0 | 0 |
| P3 | 0 | 3.59 | 0 | 0 | 0 | 0 | 0 | 0 |
| P4 | 0 | 0 | 0 | 0 | 0 | 19.99 | 0 | 0 |
| P5 | 0 | 0 | 0 | 0 | 0 | 0 | 20 | 0 |
| P6 | 0 | 0 | 0 | 20 | 0 | 0 | 0 | 0 |
| P7 | 0 | 0 | 0 | 0 | 0 | 0 | 0 | 3.01 |
| S1 | 1 | 0.13 | 0.13 | 0 | 0 | 0 | 0 | 0.15 |
| S2 | 0 | 0.12 | 0.12 | 2.51 | 2.51 | 2.49 | 2.49 | 0.12 |
| S5 | 0 | 0 | 0 | 10 | 10 | 9.99 | 10 | 0 |
| A1 | 0.1 | 0 | 0 | 3.02 | 2.8 | 2.72 | 2.51 | 0 |
| D1 | 5.14 | 2.15 | 2.15 | 63.1 | 62.97 | 62.98 | 63.02 | 1.72 |
| Total weight parts | 8.24 | 5.99 | 6 | 98.63 | 98.27 | 98.17 | 98.02 | 5.00 |
| % Si | 24.27 | 59.93 | 60.00 | 20.28 | 20.34 | 20.36 | 20.40 | 60.20 |
| Microemulsion? | yes | no | no | yes | yes | yes | yes | no |
| Dv50 (nm) | 20 | 281 | 516 | ND | ND | ND | ND | 363 |
| Dv90 (nm) | 52 | 432 | 729 | ND | ND | ND | ND | 641 |

TABLE 8

| Anionic and Cationic Emulsions | | | | |
|---|---|---|---|---|
| | Emulsion No. | | | |
| Starting Material | EM13 | EM14 | EM15 | EM18 |
| P1 | 2 | 4.8 | 0 | 3.56 |
| P3 | 0 | 0 | 3.6 | 0 |
| S1 | 0.29 | 0.24 | 0.19 | 0.2 |
| S2 | 0 | 0 | 0.13 | 0.18 |
| S3 | 2.23 | 0.76 | 0 | 0 |
| S4 | 0 | 0 | 0.42 | 0.4 |
| A1 | 0.11 | 0 | 0 | 0 |
| D1 | 2.49 | 2.21 | 1.67 | 1.58 |
| Total weight parts | 7.12 | 8.01 | 6.01 | 5.92 |
| % Si | 28.09 | 59.93 | 59.90 | 60.14 |
| Type of Emulsion | Anionic Microemulsion | Anionic | Cationic | Cationic |
| Dv50 (nm) | 16 | 213 | 176 | 198 |
| Dv90 (nm) | 24 | 423 | 309 | 453 |

In Tables 7 and 8, 'ND' means not detected.

In Table 7, emulsion EM12 was prepared as follows: 2 g of copolymer P1, 1 g of surfactant S1 and 0.7 g of water (D1) were added in a 20 DAC cup. These starting materials were speed mixed twice in a Speed Mixer at 3500 RPM, 30 seconds each time. 0.1 g of a 10% acetic acid solution (A1) was added to the cup, and the contents of the cup were speed mixed for 30 seconds at 3500 RPM. The resulting mixture was diluted stepwise with water until the final translucent/clear microemulsion was flowable (had a water-like viscosity). 0.5 g of water was added in each step and contents of the cup were speed mixed in between.

In Table 7, emulsion EM16 was prepared as follows: 3.59 g of copolymer P3, 0.13 g of surfactant S1, 0.12 g of surfactant S2, and 0.36 g of water were added in a 20 DAC cup. These starting materials were speed mixed twice in a Speed Mixer at 3500 RPM, 30 seconds each time. Water was added to the cup stepwise with speed mixing between each successive water dilution step, until the total water content was 2.15 g and the resulting emulsion was flowable.

In Table 7, emulsion sample 17 was prepared as follows: 3.6 g of copolymer P2, 0.13 g of surfactant S1, 0.12 g of surfactant S2, and 0.35 g of water were added in a 20 DAC cup. These starting materials were speed mixed twice in a Speed Mixer at 3500 RPM, 30 seconds each time. Water was added to the cup stepwise with speed mixing between each successive water dilution step until the total water content was 2.15 g and the resulting emulsion was flowable.

In Table 7, emulsions EM21-EM24 were prepared as follows: Copolymer, surfactant S5 and water (D1) were added in a 100 DAC cup. These starting materials were speed mixed in a Speed Mixer (Flaktek SpeedMixer DAC 330-100 SE) at 3500 RPM for 1 minute. The resulting mixture was diluted with the remaining amount of water (D1) stepwise with speed mixing at 3500 RPM for 30 seconds between each successive water dilution step. 10% solution of acetic acid (A1) was added to the cup, and the contents of the cup were speed mixed for 30 seconds at 3500 RPM. Surfactant S2 was then added to the cup, and the contents of the cup were speed mixed for 30 seconds at 3500 RPM.

In Table 7, emulsion EM 25 was prepared as follows: 3.01 g of copolymer P7, 0.15 g of surfactant S1, 0.12 g of S2, and 0.33 g of water were added in a 20 DAC cup. These starting materials were speed mixed twice in a Speed Mixer at 3500 RPM, 30 seconds each time. Water was added to the cup stepwise with speed mixing between each successive water dilution step until the total water content was 1.72 g, and the emulsion was flowable.

In Table 8, emulsion EM13 was prepared as follows: 2 g of copolymer P1, 0.29 g of surfactant S1 and 2.23 g of anionic surfactant S3 were added in a 20 DAC cup. These starting materials were speed mixed twice in a Speed Mixer at 3500 RPM, 30 seconds each time. 0.1 g of a 10% acetic acid solution (A1) was added to the cup, and the contents of the cup were speed mixed for 30 seconds at 3500 RPM. The resulting mixture was diluted stepwise with water until the final translucent/clear microemulsion was flowable (had a water-like viscosity). 0.5 g of water was added in each step, and the contents of the cup were speed mixed in between.

In Table 8, emulsion EM14 was prepared as follows: 4.8 g of copolymer P1, 0.24 g of surfactant S1 and 0.76 g of anionic surfactant S3 were added in a 20 DAC cup. These starting materials were speed mixed twice in a Speed Mixer at 3500 RPM, 30 seconds each time. Water was added to the cup stepwise with speed mixing between each successive water dilution until the resulting emulsion was flowable (2.21 g total).

In Table 8, emulsion EM15 was prepared as follows: 3.6 g of copolymer P3, 0.19 g of surfactant S1, 0.13 g of surfactant S2, and 0.36 g of water were added in a 20 DAC cup. These starting materials were speed mixed twice in a Speed Mixer (Flaktek SpeedMixer DAC 150.1 FVZ—K) at 3500 RPM, 30 seconds each time. Water was added to the cup stepwise until the total water content was 1.67 g. The resulting product was speed mixed between each successive water dilution step. 0.42 g of cationic surfactant S4 was added to the cup, and the contents of the cup were speed mixed for 30 seconds at 3500 RPM.

In Table 8, emulsion EM18 was prepared as follows: 3.56 g of copolymer P1, 0.2 g of surfactant S1, 0.18 g of surfactant S2, and 0.57 g of water were added in a 20 DAC cup. These starting materials were speed mixed twice in a Speed Mixer at 3500 RPM, 30 seconds each time. Water was added to the cup stepwise until the total water content was 1.58 g. The resulting product was speed mixed between each successive water dilution step. 0.4 g of cationic surfactant S4 was added to the cup, and the contents of the cup were speed mixed for 30 seconds at 3500 RPM.

Particle size of the macro-emulsions (e.g., EM14-EM18 and EM25) was measured in a Malvern Mastersizer 3000. A small amount of the emulsion (<1 wt %) was first diluted in DI water. This diluted emulsion was then added dropwise into the Hydro LV attachment of the Mastersizer until the obscuration reached 5%-8%. The particle size analysis was performed subsequently using a custom SOP for particle size less than 10 μm.

Particle size of the microemulsions (e.g., EM12 and EM13) was measured in Microtrac™ Nanotrac Wave Particle Size Analyzer. Background scattering data was collected by adding DI water to the sample chamber. A small amount of the emulsion (<1 wt %) was separately diluted in DI water. This diluted emulsion was then added dropwise into the sample chamber of the Particle Size Analyzer. The particle size analysis was performed subsequently using a custom SOP. Particle size was not detected on samples EM21-24 possibly because the actual size was below the detection limit of the instrument.

In this Reference Example 12, emulsion samples EM19 and EM20 were prepared as follows, using the starting materials and amounts shown below in Table 9. Amounts are in weight parts. The copolymer, surfactant, and first water were added in a 20 DAC cup. These starting materials were speed mixed twice in a Speed Mixer (Flaktek SpeedMixer DAC 150.1 FVZ—K) at 3500 RPM, 30 seconds each time. Acetic acid (10%) and dilution water were added to the above mixture stepwise with speed mixing between each successive water dilution step.

TABLE 9

| Emulsion Samples | | |
|---|---|---|
| | Emulsion Sample | |
| Starting Material | EM19 | EM20 |
| Copolymer sample 4a from Table 3 above | 2 | 0 |
| Copolymer sample 1f from Table 2 above | 0 | 2 |
| GENAPOL ™ UD 050, a fatty alcohol polyglycol ether from Clariant | 0.3 | 0.5 |
| GENAPOL ™ UD 110, a fatty alcohol polyglycol ether from Clariant | 0.7 | 0.5 |
| first water | 0.7 | 0.77 |
| 10% acetic acid | 0.1 | 0.11 |

TABLE 9-continued

| Emulsion Samples | | |
|---|---|---|
| | Emulsion Sample | |
| Starting Material | EM19 | EM20 |
| dilution water | 4.1 | 4.1 |
| 10% acetic acid | 0.09 | 0 |
| Total | 7.99 | 7.98 |

In this Comparative Example 13, an aminosilicone emulsion (EM11) was prepared as follows: 57.5 g of Bis-Diisopropanolamino-PG-Propyl Disiloxane/Bis-Vinyl Dimethicone Copolymer, 2.4 g of T Maz-20, and 6 g of water were added in a 100 DAC cup. These starting materials were speed mixed twice in a Speed Mixer (Flaktek SpeedMixer DAC 150.1 FVZ—K) at 3500 RPM, 30 seconds each time. 12 g of water was added to the cup, and the contents of the cup were speed mixed in the Speed Mixer at 3500 RPM. An additional 22 g of water was added to the cup, and the contents of the cup were speed mixed in the Speed Mixer at 3500 RPM.

In this Reference Example 14, rinse off hair conditioner formulations (CF) were prepared using the emulsions prepared as described above and the starting materials shown below in Table 10.

TABLE 10

| Rinse Off Hair Conditioner Formulation Starting Materials | | |
|---|---|---|
| Starting Material | Description | Source |
| Thickening Agent (HEC) | Hydroxyethyl Cellulose | Cellosize ™ hydroxyethyl cellulose PCG-10 Europe from TDCC |
| TS-EDTA | Tetrasodium Ethylenediaminetetraacetic acid | Versene ™ 220 crystals from TDCC |
| Oil | Cetearyl alcohol | Crodacol ™ CS-50 from Croda |
| Additional Emulsifier (Stear.) | PEG-100 Stearate & Glyceryl Stearate | Arlacel ™ 165 from Croda |
| Conditioning Agent (8500) | Bis (C13-15 Alkoxy) PG Amodimethicone | DOWSIL ™ 8500 Conditioning Agent from DSC |
| DOWSIL ™ 5-7113 Silicone Quat MicroEmulsion | Silicone Quaternium-16 (and) Undeceth-11 (and) Butyloctanol (and) Undeceth-5 | DOWSIL ™ 5-7113 Silicone Quat MicroEmulsion (22% silicone) from DSC |
| PE | Phenoxyethanol and Methylisothiazolinone | Neolone ™ PE preservative from source DuPont |
| CE-7080 | Silicone Quaternium-16/Glycidoxy Dimethicone Crosspolymer and Undeceth-11 and Undeceth-5 | DOWSIL ™ CE-7080 Smart Style |
| EM1 | Terminal aminosilicone with 319 DP | |
| EM2 | Terminal aminosilicone with 44 DP | |

Samples of Rinse Off Hair Conditioner Formulations were prepared as follows, using the amounts of each starting material shown in Table 11, below. Deionized water was added to a mixing vessel and heated to 70° C. With moderate agitation, the hydroxyethyl cellulose was dispersed until fully dissolved. Heat was decreased to 60° C. and cetearyl alcohol and PEG-100 stearate and glyceryl stearate and silicone (if any) were added. The conditioner was mixed for 3 minutes and then tetrasodium EDTA was added and mixed for 3 minutes. When the temperature was below 40° C., the phenoxyethanol was added. The water loss was compensated for and the resulting formulation was mixed for an additional 5 minutes. The final pH of the conditioner formulations were all approximately 5.

For silicone emulsion, the emulsion was added at the end together phenoxyethanol.

TABLE 11

Comparative Hair Conditioner Formulations

| | | | | | | | |
|---|---|---|---|---|---|---|---|
| Phase C | PE | | 0.5 | 0.5 | 0.5 | 0.5 | 0.5 |
| | EM | 6 | 0 | 0 | 0 | 0 | 0 |
| | EM | 5 | 0 | 0 | 0 | 0 | 0 |
| | EM | 4 | 0 | 0 | 0 | 0 | 0 |
| | EM | 3 | 0 | 0 | 0 | 0 | 0 |
| | EM | 2 | 0 | 0 | 0 | 0 | 4 |
| | EM | 1 | 0 | 0 | 0 | 1.67 | 0 |
| | 5-7113 | | 0 | 4.5 | 0 | 0 | 0 |
| Phase B | 8500 | | 0 | 0 | 0 | 0 | 0 |
| | Stear. | | 1 | 1 | 1 | 1 | 1 |
| | Oil | | 1 | 1 | 1 | 1 | 1 |
| Phase A | $H_2O$ | | qs | qs | qs | qs | qs |
| | TS-EDTA | | 0.2 | 0.2 | 0.2 | 0.2 | 0.2 |
| | HEC | | 1.4 | 1.4 | 1.4 | 1.4 | 1.4 |
| | Starting Material/CF No. | | CF1 | CF2 | CF3 | CF4 | CFS |
| | | | Comparative Example | | | | |

| | | | | | | | | | | | | | |
|---|---|---|---|---|---|---|---|---|---|---|---|---|---|
| Phase C | PE | | 0.5 | 0.5 | 0.5 | 0.5 | 0.5 | 0.5 | 0.5 | 0.5 | 0.5 | 0.5 | 0.5 |
| | EM 25 | | 0 | 0 | 0 | 0 | 0 | 0 | 0 | 0 | 0 | 0 | 1.67 |
| | EM 20 | | 0 | 0 | 0 | 0 | 0 | 0 | 0 | 0 | 0 | 4 | 0 |
| | EM 19 | | 0 | 0 | 0 | 0 | 0 | 0 | 0 | 0 | 4 | 0 | 0 |
| | EM | 10 | 0 | 0 | 0 | 0 | 0 | 0 | 0 | 4 | 0 | 0 | 0 |
| | EM | 9 | 0 | 0 | 0 | 0 | 0 | 0 | 1.67 | 0 | 0 | 0 | 0 |
| | EM | 8 | 0 | 0 | 0 | 0 | 0 | 4 | 0 | 0 | 0 | 0 | 0 |
| | EM | 7 | 0 | 0 | 0 | 0 | 1.67 | 0 | 0 | 0 | 0 | 0 | 0 |
| | EM | 6 | 0 | 0 | 0 | 1.67 | 0 | 0 | 0 | 0 | 0 | 0 | 0 |
| | EM | 5 | 0 | 0 | 1.67 | 0 | 0 | 0 | 0 | 0 | 0 | 0 | 0 |
| | EM | 4 | 0 | 1.67 | 0 | 0 | 0 | 0 | 0 | 0 | 0 | 0 | 0 |
| | EM | 3 | 1.67 | 0 | 0 | 0 | 0 | 0 | 0 | 0 | 0 | 0 | 0 |
| | EM | 2 | 0 | 0 | 0 | 0 | 0 | 0 | 0 | 0 | 0 | 0 | 0 |
| | EM | 1 | 0 | 0 | 0 | 0 | 0 | 0 | 0 | 0 | 0 | 0 | 0 |
| Phase B | Stear. | | 1 | 1 | 1 | 1 | 1 | 1 | 1 | 1 | 1 | 1 | 1 |
| | Oil | | 1 | 1 | 1 | 1 | 1 | 1 | 1 | 1 | 1 | 1 | 1 |
| Phase A | $H_2O$ | | qs | qs | qs | qs | qs | qs | qs | qs | qs | qs | qs |
| | TS-EDTA | | 0.2 | 0.2 | 0.2 | 0.2 | 0.2 | 0.2 | 0.2 | 0.2 | 0.2 | 0.2 | 0.2 |
| | HBC | | 14 | 1.4 | 1.4 | 1.4 | 1.4 | 1.4 | 1.4 | 1.4 | 1.4 | 1.4 | 1.4 |
| | Starting Material/CF No. | | CF6 | CF7 | CF8 | CF9 | CF1 | CF11 | CF12 | CF13 | CF14 | CF15 | CF16 |
| | | | Inventive Examples | | | | | | | | | | |

In Table 11 qs is "quantity sufficient".

Studies to evaluate ease of wet and dry combing of hair treated with a rinse off hair conditioner formulation (CF1-CF13 described above) were performed as follows. Slightly bleached Caucasian hair from International Hair Importers was used for testing the rinse off hair conditioner formulations. Each tress weighed 2 grams. Each tress was rinsed for 30 seconds under a stream of 40° C. tap water. Using a pipette, 0.4 grams of a solution containing nine percent of sodium lauryl sulfate was applied and lathered through each tress for 30 seconds. The tresses were then rinsed for 1 minute under running water. Excess water was removed from the tresses by passing each tress between the index and middle fingers of the hand. The tresses were then treated with a rinse off hair conditioner formulation of one of Examples CF1-CF13 at 0.4 g formulation/g of hair by massaging the formulation into the wet/damp hair for 1 minute. The tresses were then rinsed for 30 seconds under tap water at 40° C. Excess water was removed by pulling the tresses through the index and middle fingers of the hand. The tresses were placed on a tray covered with paper towels and dried overnight at room temperature. The rinse off hair conditioner samples prepared as described in Reference Example 14, above, were tested according to the COEFFICIENT OF FRICTION, INSTRON COMBING, INSTRON WET COMBING, and INSTRON DRY COMBING methods described below. The results are shown below in Table 12.

TABLE 12

Rinse Off Hair Condition Formulation Combing and Friction Results

| Sample | | Dry ACL (kgf) | Dry ACL std | Wet ACL (kgf) | Wet ACL std | COF | COF std |
|---|---|---|---|---|---|---|---|
| Comparative Example | CF1 | 0.041 | 0.019 | 1.009 | 0.285 | 0.751 | 0.070 |
| Comparative Example | CF2 | 0.018 | 0.002 | 0.025 | 0.004 | 0.187 | 0.025 |
| Comparative Example | CF3 | 0.018 | 0.002 | 0.044 | 0.005 | 0.211 | 0.022 |

TABLE 12-continued

| Rinse Off Hair Condition Formulation Combing and Friction Results | | | | | | | |
|---|---|---|---|---|---|---|---|
| Sample | | Dry ACL (kgf) | Dry ACL std | Wet ACL (kgf) | Wet ACL std | COF | COF std |
| Comparative Example | CF4 | 0.013 | 0.002 | 0.051 | 0.005 | 0.175 | 0.005 |
| Comparative Example | CF5 | 0.015 | 0.001 | 0.039 | 0.004 | 0.343 | 0.023 |
| Inventive Example | CF6 | 0.018 | 0.001 | 0.040 | 0.005 | 0.320 | 0.013 |
| Inventive Example | CF7 | 0.014 | 0.001 | 0.030 | 0.002 | 0.313 | 0.007 |
| Inventive Example | CF8 | 0.014 | 0.002 | 0.026 | 0.003 | 0.291 | 0.008 |
| Inventive Example | CF9 | 0.017 | 0.003 | 0.034 | 0.002 | 0.285 | 0.009 |
| Inventive Example | CF10 | 0.019 | 0.004 | 0.041 | 0.008 | 0.251 | 0.011 |
| Inventive Example | CF11 | 0.013 | 0.001 | 0.038 | 0.004 | 0.338 | 0.007 |
| Inventive Example | CF12 | 0.014 | 0.002 | 0.035 | 0.004 | 0.210 | 0.005 |
| Inventive Example | CF13 | 0.011 | 0.001 | 0.028 | 0.006 | 0.240 | 0.021 |
| Inventive Example | CF16 | 0.017 | 0.002 | 0.027 | 0.004 | 0.223 | 0.009 |

Comparative example 1 was the control, which contained no copolymer and no terminal aminosilicone comparative. Comparative examples 2 and 3 contained commercially available aminosilicones instead of a copolymer of the present invention.

The results in Table 12 showed that all inventive examples containing the copolymer made using a terminal primary aminofunctional siloxane performed significantly better than the control CF1 in both dry and wet combing. While most inventive copolymers performed on par with the comparative commercial aminosilicones, CF13 outperformed other polymers in dry combing. For COF, all samples performed better than CF1, the control.

In this Reference Example 15, hair care compositions CF17-CF23 were prepared, and styling/curl retention was evaluated as follows: CF17-23 were prepared by simply diluting the emulsion in deionized water at room temperature with an adequate agitation. Samples CF17-CF23 had the starting materials in the amounts in Table 13, below. Amounts are in weight parts.

Studies to evaluate styling and curl retention benefits formulation of Examples CF17-CF23 were performed as follows. Slightly bleached Caucasian hair from International Hair Importers was used for testing. Each tress weighed 2 grams. Each tress was rinsed for 30 seconds under a stream of 40° C. tap water. Using a pipette, 0.4 grams of a solution containing nine percent of sodium lauryl sulfate was applied and lathered through each tress for 30 seconds. The tresses were then rinsed for 1 minute under running water. Excess water was removed from the tresses by passing each tress between the index and middle fingers of the hand. The tresses were then treated with a one of Samples CF17-CF21 at 0.15 g formulation/g of hair by massaging the formulation into the wet/damp hair for 1 minute. The tresses were wrapped tightly on curler and left in 45° C. oven overnight. Next day, the tresses were removed from the oven and cool to room temperature for 30 min. The curlers were carefully removed from the tresses, and the tresses were hung in the humidity chamber at 25° C., 80% relative humidity for a total of 5 hours. The curl retention (%) was calculated based on the length of the tresses prior to incubating in the humidity chamber. Results from Table 13 show that hair treated with CF20 and CF21 provided improved curl retention in comparison to the comparative examples CF17 and CF18 and on par with the top silicone performer (CF19).

TABLE 13

| Samples CF17-CF23 Preparation and Styling/Curl Retention Testing Results | | | | | | | |
|---|---|---|---|---|---|---|---|
| | CF17 | CF18 | CF19 | CF20 | CF21 | CF22 | CF23 |
| Water | 100 | q.s. | q.s. | q.s. | q.s. | q.s. | q.s. |
| EM11 (from Comparative Example 13) | 0 | 3.45 | 0 | 0 | 0 | 0 | 0 |
| Silicone Quaternium-16/Glycidoxy Dimethicone Crosspolymer and Undeceth-11 and Undeceth-5 (25% silicone active)[a] | 0 | 0 | 8 | 0 | 0 | 12 | 0 |
| EM19 | 0 | 0 | 0 | 3.33 | 0 | 0 | 0 |
| EM20 | 0 | 0 | 0 | 0 | 3.33 | | 5 |

In Table 13, q.s means "Quantity sufficient".

[a]Available from DSC under the trade name DOWSIL ™ CE-7080 Smart Style, used in comparative examples.

TABLE 14

| Curl retention (%) after 5 hours incubation at 25° C., 80% relative humidity | | |
|---|---|---|
| Sample | % CURL RETENTION @ 5 hrs | Standard deviation |
| CF17 | 18.96 | 4.5 |
| CF18 | 23.37 | 2.7 |
| CF19 | 31.52 | 0.21 |
| CF20 | 25.04 | 0.11 |
| CF21 | 30.22 | 2.8 |

CF 21 contains a copolymer with a longer degree of polymerization (DP) and performs on par with the comparative sample CF19. However, it is known that the polymer used in CF19 contains a high level of cyclomethicone (>0.1%) which has been a concern in personal care applications. The polymers used in CF20 and CF21 have low level of cyclomethicone (<0.1%) even after aging at room temperature for 2 years. The inventors surprisingly found that the copolymer of this invention had the benefit of low cyclomethicone content, particularly in the sample with a longer DP siloxane. When using a shorter DP siloxane in the copolymer (CF20-EM19 with 44 DP siloxane), the curl retention benefit was also observed when compared to the control.

In this Reference Example 16, hair alignment was evaluated as follows: Frizzy hair purchased from International Hair was washed with 9% SLS for 30 seconds and treated with 0.15 g of CF17, CF22, or CF23 per gram of hair. The tresses were left at room temperature, 50% relative humidity, the alignment coefficient was measured using RUMBA by Bossa Nova after 3 and 21 hours with and without combing. The results, below in Table 15, showed that the tresses treated with an inventive example (CF23) has a higher hair alignment in comparison to control in all conditions. When compared to the comparative example CF22, hair treated with CF23 showed a significant improved alignment after 21 h.

TABLE 15

| Hair Alignment | | | | |
|---|---|---|---|---|
| | Measurement | Comparative | | Inventive |
| | Condition | CF17 | CF22 | CF23 |
| Alignment Coefficient as measured by Rumba | 3 h, no combing | 9.87 | 15.3 | 13.65 |
| | 21 h, no combing | 11.94 | 9.86 | 14.89 |
| | 21 h, after combing | 10.52 | 11.66 | 15.55 |

The test methods used in herein are as described below.

$^{29}$Si NMR and $^{13}$C NMR spectroscopy can be used to quantify the hydrocarbon group (e.g., R group, such as $R^8$ and/or $R^9$ described above) content in a polydiorganosiloxane. A $^{29}$Si NMR spectrum should be acquired using the methodology outlined by Taylor et. al. in Chapter 12 of *The Analytical Chemistry of Silicones*, ed. A. Lee Smith, Vol. 112 in Chemical Analysis, John Wiley & Sons, Inc. (1991), pages 347-417, and section 5.5.3.1. In this chapter, the authors discuss general parameters unique to acquiring quantitative NMR spectra from Silicon nuclei. Each NMR spectrometer is different with respect to the electronic components, capabilities, sensitivity, frequency and operating procedures. One should consult instrument manuals for the spectrometer to be used in order to tune, shim and calibrate a pulse sequences sufficient for quantitative 1D measurement of $^{29}$Si and $^{13}$C nuclei in a sample.

A key output of a NMR analysis is the NMR spectrum. Without standards, it is recommended that the signal to noise ratio of signal height to average baseline noise be no less than 10:1 to be considered quantitative. A properly acquired and processed NMR spectrum results in signals that can be integrated using any commercially available NMR processing software package.

From these integrations, the weight percent of total R group content can be calculated from the $^{29}$Si NMR spectrum according to the following: $(I^M)\cdot(U^M)=G^M$; $(I^{M(R)})\cdot(U^{M(R')})=G^{M(R)}$; $(I^D)\cdot(U^D)=G^D$; $(I^{D(R)})\cdot(U^{D(R)})=G^{D(R)}$; $U^R/U^{M(R)}=Y^{R'}$; $U^R/U^{D(R)}=Y^{R''}$; $Y^{R''}\cdot[G^{M(R)}/(G^M+G^{M(R)}+G^D+G^{D(R)})\cdot 100]=W^{R'}$; $Y^{R'''}\cdot[G^{D(R)}/(G^M+G^{M(R)}+G^D+G^{D(R)})\cdot 100]=W^{R''}$; and $W^{R'}+W^{R''}$=TOTAL $W^R$; where I is the integrated signal of the indicated siloxy group; U is the unit molecular weight of the indicated siloxy group; G is a placeholder representing the grams unit; W is the weight percent of the indicated siloxy unit; Y is a ratio value for the specified siloxy unit; R is as described above; R' represents R groups only from M(R); and R" represents R groups only from D(R) groups.

$^1$H-NMR was evaluated using a Varian 400 MHz Mercury NMR Spectrometer. Samples were prepared by dissolving the analyte in $CDCl_3$ where the $CDCl_3$ consisted of at least 60% of the mass but no more than 90%. Determination of complete conversion of acrylate components was made when the vinyl proton signals could not be discerned from the baseline.

FTIR can be used to determine the concentration of unreacted acrylate present in the $(AB)_n$ co-polymers. FTIR analysis was conducted using a PerkinElmer FTIR Spectrometer Frontier. Samples were prepared by diluting the polymers in tetrachloroethylene and mixing with a vortex measure. Once mixed, the sample was pipetted into a FTIR sample cell with a fixed gap between two NaCl salt plates. The sample cell was then placed in the FTIR instrument and scanned 16 times to produce the final spectra.

Rheometry can be used to measure the viscosity of the co-polymers. Viscosity measurements were conducted on a Brookfield DV-III Ultra Programmable Rheometer fitted with a CPE-52 cone and a CPE-44Y standard sample cup with integrated temperature probe and calibrated to measure the dynamic viscosity of amino silicone polymers as described in the manual. Approximately 0.4 mL of sample was syringed into the center of the sample cup and the sample cup set into place for a measurement. The temperature of the cup was confirmed to be 25° C. and the appropriate RPM value was determined by examining the % torque and adjusting the RPM value as needed.

GPC can be used to measure the number averaged molecular weight (Mn) and weighted average molecular weight (Mw) of the copolymers. Measurements were conducted using the system described in the table below. The samples were prepared at 10 mg/mL concentration in 20 mL scintillation vials and capped with acetic anhydride. The samples were shaken using a wrist shaker for 2 hours prior to being filtered through 0.45 μm PTFE syringe filters into 2 mL GC vials. The samples were placed on the autosampler and data collection started. Data collection occurred over 30 minutes and the data were processed and analyzed against polystyrene standards ranging from 580 to 2,750,000 Daltons.

| | |
|---|---|
| Sample Prep | 10 mg/ml in certified grade THF; filtered through 0.45 μm PTFE syringe filters prior to injection |
| Pump | Waters e2695 LC Pump |
| Eluent | Fisher Scientific HPLC grade THF |
| Flow Rate | 1.0 mL/min |
| Injector | Waters 2695; 100 μL injection |
| Columns | Two Polymer Labs 5 μm Mixed C columns; held at 35° C. |
| Detection | Shodex model RI-501 differential refractive index detector held at 35° C. |
| Data System | Polymer Labs Cirrus version 3.3 |
| Calibration | 16 narrow polystyrene standards from Polymer labs, fit to a 3rd order polynomial curve over the range of 2,750 kg/mol to 0.580 kg/mol. |

COEFFICIENT OF FRICTION is an industry standard method for measuring reduced frictional properties of treatments on hair and correlates with sensory attributes for smoothness and softness. A Diastron MTT175 tensile tester with 50 g normal force mounted on rubber probe was used for testing in a temperature and humidity controlled room. Three tresses per treatment and 5 measurements per tress were tested to generate the friction data both with and against the hair cuticles. Coefficient of friction (COF)=F/N, where F was the externally applied force and N was the normal force. The same tresses from the combing study were used for measuring the coefficient of friction in the dry state.

An INSTRON Model 4464 running BlueHill 2 Software was used for determining conditioning performance by the ease of wet combing and the ease of dry combing. The test employed an INSTRON strain gauge, which was equipped to measure the force required to comb the hair. The conditioning performance was based on the ability of a particular hair treatment formulation, such as a shampoo or a hair conditioner, to reduce the force required to comb the hair with the INSTRON strain gauge. The force was reported as an Average Combing Load (ACL). The lower the number of the ACL value, the better was the conditioning effect imparted by the formulation being tested.

According to the INSTRON WET COMBING method, hair was first wetted by dipping it into distilled water, and then the hair was detangled by combing the tress three times. The tress was then retangled by dipping in distilled water three times. Excess water was removed by passing the tress through the index and middle fingers of the hand twice. The tress was placed on a hanger and INSTRON combed. Retangling and INSTRON combing were repeated until all data points are collected. An average combing force of three tresses was measured for each treatment.

According to the INSTRON DRY COMBING method, hair was detangled by combing the tress 3 times. Then hair was retangled by swirling the tress clockwise 3 times and swirling it counter clockwise 3 times. The tress was then placed on a hanger and INSTRON combed. Retangle and Instron combing were repeated until all data points were collected. An average combing force for three tresses was measured for each treatment.

INDUSTRIAL APPLICABILITY

The copolymer described here may have one or more of the following advantages: low cyclic polyorganosiloxane content (<0.05% octamethylcyclotetrasiloxane), stability after aging as evidenced by low cyclics content after aging, little or no crosslinking, and potential for biodegradability. Furthermore, the copolymer may be miscible with organic solvents and some oils. Without wishing to be bound by theory, it is thought that using a copolymer in which subscript a is at least 44, alternatively 44 to 200, alternatively 44 to 84 may provide improved curl retention when formulated into a hair styling composition. Without wishing to be bound by theory, it is further thought that $R^D$ with longer chain (e.g., >6 carbon atoms, alternatively 10 or more carbon atoms, may improve performance of the copolymer on hair, particularly for the dry combing test described above. As shown by the examples above, the copolymers of this invention also provide significantly better wet combing performance than terminal aminosilicone polymers using the wet combing test described above.

The copolymer described herein is useful in hair care applications and may provide one or more benefits in styling such as increased curl retention, improved hair alignment, and/or improved hair orientation and/or hair conditioning, as evidenced by improved dry and/or wet combing performance and improved coefficient of friction.

DEFINITIONS AND USAGE OF TERMS

All amounts, ratios, and percentages are by weight unless otherwise indicated by the context of the specification. The amounts of all starting materials in a composition total 100% by weight. The SUMMARY and ABSTRACT are hereby incorporated by reference. The articles ‘a’, ‘an’, and ‘the’ each refer to one or more, unless otherwise indicated. The singular includes the plural unless otherwise indicated. The terms “comprising” or “comprise” are used herein in their broadest sense to mean and encompass the notions of “including,” “include,” “consist(ing) essentially of,” and “consist(ing) of. The use of “for example,” “e.g.,” “such as,” and “including” to list illustrative examples does not limit to only the listed examples. Thus, “for example” or “such as” means “for example, but not limited to” or “such as, but not limited to” and encompasses other similar or equivalent examples. The disclosure of ranges includes the range itself and also anything subsumed therein, as well as endpoints. Similarly, the disclosure of Markush groups includes the entire group and also any individual members and subgroups subsumed therein. For example, disclosure of the Markush group a hydrogen atom, an alkyl group, an alkenyl group, or an aryl group, includes the member alkyl individually; the subgroup alkyl and aryl; and any other individual member and subgroup subsumed therein. Abbreviations are as defined below in Table 7.

TABLE 7

Abbreviations

| Abbreviation | Definition |
|---|---|
| ° C. | degrees Celsius |
| DI Water | deionized water |
| DP | average degree of polymerization |
| DSC | Dow Silicones Corporation of Midland, Michigan, USA |
| Dv | Volume median diameter |
| g | gram |
| GPC | gel permeation chromatography |
| hrs or h | hour |
| IR | infra-red spectroscopy |
| Kgf or kgf | kilogram force |
| ml or mL | milliliters |
| Mn | number average molecular weight. Mn may be measured using GPC. |
| mPa · s | milliPascal second |
| NMR | nuclear magnetic resonance |
| ppm | part per million |
| qs or q.s. | quantity sufficient |
| RPM or rpm | revolutions per minute |
| RT | room temperature of 23° C. ± 2° C. |
| s | second |
| TDCC | The Dow Chemical Company of Midland, Michigan, USA |

The invention claimed is:

1. An aminosiloxane ester copolymer comprises formula:

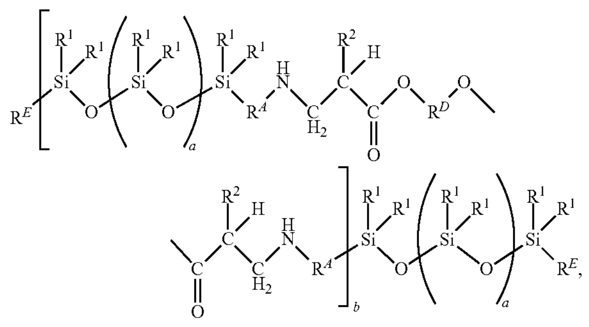

where each $R^1$ is an independently selected monovalent hydrocarbon group of 1 to 12 carbon atoms, each $R^E$ is independently selected from the group consisting of hydroxyl and an amino-functional group of formula $H_2N—R^A—$, each $R^A$ is an independently selected divalent hydrocarbon group of 1 to 12 carbon atoms, each $R^2$ is independently selected from the group consisting of hydrogen and methyl, each $R^D$ is an independently selected divalent hydrocarbon group of 2 to 20 carbon atoms, each subscript a independently has a value such that $0 \le a < 220$, and subscript b has a value such that $1 \le b \le 100$.

2. The copolymer of claim 1, where one or more of conditions i) to vii) are satisfied, where condition i) is that subscript a is 2 to 200; condition ii) is that subscript b is 2 to 20; condition iii) is that each $R^D$ has 3 to 12 carbon atoms; condition iv) is that each $R^2$ is hydrogen; condition v) is that each $R^1$ is an alkyl group of 1 to 6 carbon atoms; condition vi) is that each $R^A$ is an alkyl group of 1 to 6 carbon atoms; and condition vii) is that the copolymer has a number average molecular weight of >1,000 g/mole to 250,000 g/mol measured by gel permeation chromatography.

3. The copolymer of claim 1, where subscript a has value of 16 to 84.

4. An emulsion comprising:

(I) a liquid continuous phase comprising water, and (II) a discontinuous phase dispersed in the liquid continuous phase, where the discontinuous phase comprises the aminosiloxane ester copolymer of claim 1.

5. The emulsion of claim 4, where the emulsion further comprises an additional starting material selected from the group consisting of (H) a surfactant, (I) an acid compound, (J) an acid anhydride, (K) a thickener, (L) a stabilizer, and a combination of two or more of (H), (I), (J), (K), and (L).

6. A process for preparing the copolymer of claim 1, where each $R^E$ is the amino-functional group, and where the process comprises:

1) Combining starting materials comprising (A) a terminal primary amino-functional polyorganosiloxane of formula

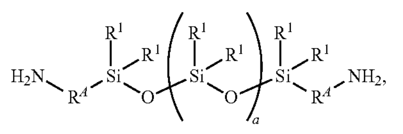

where each $R^1$ is an independently selected monovalent hydrocarbon group of 1 to 12 carbon atoms, each $R^A$ is an independently divalent hydrocarbon group of 1 to 12 carbon atoms, subscript a has a value such that $0 \le a < 220$; and (B) a bis-acryloyloxy-alkane of formula

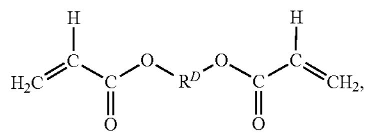

where $R^D$ is a divalent hydrocarbon group of 2 to 20 carbon atoms;

where starting material (A) and starting material (B) are present in amounts such that a molar ratio of (A):(B) ranges from 2:1 to 1:1.1.

7. The process of claim 6, where (B) the bis-acryloyloxy-alkane is selected from the group consisting of 1,3-butanediol diacrylate; 1,4-butanediol diacrylate; 1,6-hexanediol diacrylate; 1,9-nonanediol diacrylate; 1,10-decanediol diacrylate; and a combination of two or more of 1,3-butanediol diacrylate; 1,4-butanediol diacrylate; 1,6-hexanediol diacrylate; 1,9-nonanediol diacrylate; and 1,10-decanediol diacrylate.

8. The process of claim 6, further comprising adding, during step 1), an additional starting material selected from the group consisting of: (C) a catalyst, (D) a solvent, (E) an acrylate polymerization inhibitor, and a combination of two or more of (C), (D), and (E).

9. The process of claim 6, where one or both of conditions (a) and (b) is satisfied, where condition (a) is that combining in step 1) comprises mixing and heating the starting materials at a temperature of 0° C. to 180° C.; and condition (b) is that combining in step 1) is performed for 1 to 48 hours.

10. The process of claim 6, further comprising: 2) recovering the copolymer during and/or after step 1).

11. A process for preparing the copolymer of claim 1, wherein the process comprises:

1) Combining starting materials comprising:

(B) a bis-acryloyloxy-alkane of formula

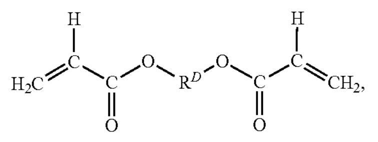

where $R^D$ is a divalent hydrocarbon group of 2 to 20 carbon atoms;

(F) a bis-silanol-terminated polydiorganosiloxane of formula:

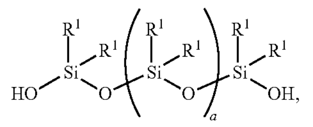

where $R^1$ is an independently selected monovalent hydrocarbon group of 1 to 12 carbon atoms, and subscript a independently has a value such that $0 \le a < 220$;

(G) a cyclic siloxazane of formula

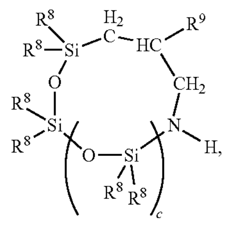

where subscript c is 0 or 1, each $R^8$ is an independently selected monovalent hydrocarbon group of 1 to 18 carbon atoms, each $R^9$ is independently selected from the group consisting of hydrogen and an alkyl group of 1 to 15 carbon atoms.

12. The process of claim 11, where less than 2 molar equivalents of (G) the cyclic siloxazane, per mole of (F) the bis-silanol-terminated polydiorganosiloxane are used in the process.

13. The process of claim 11, where 2 or more molar equivalents of (G) the cyclic siloxazane, per mole of (F) the bis-silanol-terminated polydiorganosiloxane are used in the process.

14. The process of claim 11, where (B) the bis-acryloyloxy-alkane is selected from the group consisting of 1,3-butanediol diacrylate; 1,4-butanediol diacrylate; 1,6-hexanediol diacrylate; 1,9-nonanediol diacrylate; 1,10-decanediol diacrylate; and a combination of two or more of 1,3-butanediol diacrylate; 1,4-butanediol diacrylate; 1,6-hexanediol diacrylate; 1,9-nonanediol diacrylate; and 1,10-decanediol diacrylate.

15. The process of claim 11, further comprising adding, during step 1), an additional starting material selected from the group consisting of: (C) a catalyst, (D) a solvent, (E) an acrylate polymerization inhibitor, and a combination of two or more of (C), (D), and (E).

16. The process of claim 11, where one or both of conditions (a) and (b) is satisfied, where condition (a) is that combining in step 1) comprises mixing and heating the starting materials at a temperature of 0° C. to 180° C.; and condition (b) is that combining in step 1) is performed for 1 to 48 hours.

17. The process of claim 11, further comprising: 2) recovering the copolymer during and/or after step 1).

18. A method for preparing an emulsion, the method comprising: mixing under shear starting materials comprising the copolymer of claim 1, water, and optionally one or more starting material selected from the group consisting of (H) a surfactant, (I) an acid compound, (J) an acid anhydride, (K) a thickener, and (L) a stabilizer.

19. A method comprising: applying a hair care composition to hair, wherein the hair care composition comprises the copolymer of claim 1.

20. The method of claim 19, where the hair care composition is a conditioner or a styling product.

* * * * *